United States Patent [19]
Wright et al.

[11] Patent Number: 4,939,265
[45] Date of Patent: Jul. 3, 1990

[54] INTERMEDIATES AND PROCESS FOR THE PREPARATION OF ANTIHYPERCHOLESTEROLEMIC TETRAZOLE COMPOUNDS

[75] Inventors: John J. Wright, Middletown; Sing-Yuen Sit, Meriden; Neelakantan Balasubramanian, Bristol; Peter J. Brown, Cromwell, all of Conn.

[73] Assignee: Bristol-Myers Company, New York, N.Y.

[21] Appl. No.: 430,029

[22] Filed: Nov. 1, 1989

Related U.S. Application Data

[60] Division of Ser. No. 151,512, Feb. 18, 1988, Pat. No. 4,898,949, which is a continuation-in-part of Ser. No. 18,558, Feb. 25, 1987, abandoned.

[51] Int. Cl.$^5$ .................... C07F 9/28; C07F 9/65
[52] U.S. Cl. ........................................ 548/112
[58] Field of Search ........................................ 548/112

[56] References Cited

U.S. PATENT DOCUMENTS 4,784,993 11/1988 Bogles ........................... 548/112 X
4,870,187 9/1989 Sit et al. ........................ 548/112 X Primary Examiner—David B. Springer
Attorney, Agent, or Firm—Aldo A. Algieri

[57] ABSTRACT

This invention provides novel tetrazole intermediates of the formula

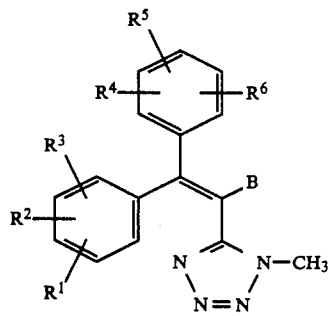

wherein
$R^1$ and $R^4$ each are independently hydrogen, halogen, $C_{1-4}$alkyl, $C_{1-4}$alkoxy or trifluoromethyl;
$R^2$, $R^3$, $R^5$ and $R^6$ each are independently hydrogen, halogen, $C_{1-4}$alkyl or $C_{1-4}$alkoxy;
B is hydrogen, $C_{1-4}$alkoxycarbonyl, $CH_2Y$ or $CH_2Z$;
Y is hydrogen, hydroxyl or X;
Z is

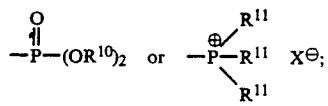

X is bromo, chloro or iodo;
$R^{10}$ is $C_{1-4}$alkyl; and
$R^{11}$ is phenyl which is unsubstituted or substituted by one or two $C_{1-4}$alkyl or chloro substituents.

and processes thereof which are useful for the preparation of antihypercholesterolemic agents.

11 Claims, No Drawings

INTERMEDIATES AND PROCESS FOR THE PREPARATION OF ANTIHYPERCHOLESTEROLEMIC TETRAZOLE COMPOUNDS

CROSS-REFERENCE TO RELATED APPLICATIONS

This application is a divisional of our co-pending application Ser. No. 151,512, filed Feb. 18, 1988, U.S. Pat. No. 4,898,949, which is a continuation-in-part of Ser. No. 018,558, filed Feb. 25, 1987, abandoned.

BACKGROUND OF THE INVENTION

1. Field of the Invention

The present invention relates to novel tetrazole intermediates which are useful for the preparation of novel inhibitors of the enzyme 3-hydroxy-3-methylglutaryl coenzyme A (HMG-CoA) reductase, which are useful in the treatment of hypercholesterolemia, hyperlipoproteinemia and atherosclerosis. The present invention also provides processes for the preparation and use of the tetrazole intermediates.

2. Disclosure Statement

The natural fermentation products Compactin (R=H) disclosed by A. Endo, et al. in Journal of Antibiotics, 29, 1346–1348 (1976) and Mevinolin (R=CH$_3$) disclosed by A. W. Alberts, et al. in J. Proc. Natl. Acad. Sci. U.S.A., 77, 3957 (1980) are very active antihypercholesterolemic agents which limit cholesterol biosynthesis by inhibiting the enzyme HMG-CoA reductase, the rate-limiting enzyme and natural point of cholesterogenesis regulation in mammals, including man. Compactin (R=H) and Mevinolin (R=CH$_3$; also known as lovastatin) have the structures shown below:

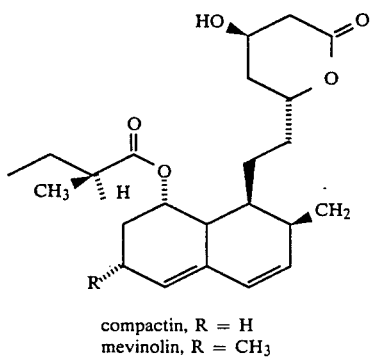

compactin, R = H
mevinolin, R = CH$_3$

A number of structurally related synthetic compounds useful in the treatment of hypercholesterolemia have also been disclosed in patents and other publications. The synthetic art most closely related is as follows:

U.S. Pat. No. 4,198,425, issued Apr. 15, 1980 to S. Mistui, et al. describes novel mevalonolactone derivatives useful for the treatment of hyperlipidemia and having the general formula

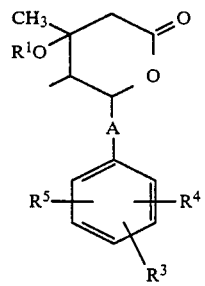

wherein A represents a direct linkage, methylene, ethylene, trimethylene or vinylene group and R$^3$, R$^4$ and R$^5$ represent various substituents.

European patent application No. EP-24,348 published Mar. 4, 1981 discloses new hypocholesterolemic and hypolipemic compounds having the structure

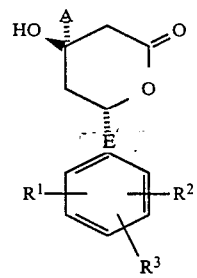

wherein A is H or methyl; E is a direct bond, —CH$_2$—, —(CH$_2$)$_2$—, —(CH$_2$)$_3$— or —CH=CH—; R$^1$, R$^2$ and R$^3$ each represent various substituents and the corresponding dihydroxy acids resulting from the hydrolytic opening of the lactone ring.

U.S. Pat. No. 4,375,475, issued Mar. 1, 1983 to A. K. Willard, et al. discloses essentially the same structures and is concordant to the above-mentioned EP-24,348 patent application.

European patent application No. EP-68,038 published Jan. 5, 1983 discloses and claims the resolved trans-enantiometer, process for its preparation and pharmaceutical composition thereof having the structure

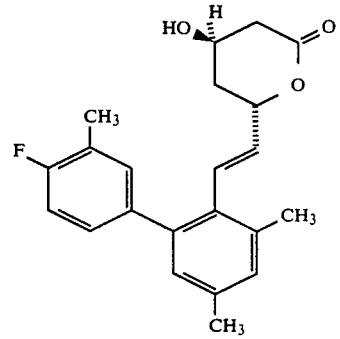

and the corresponding dihydroxy acid, or a pharmaceutically acceptable salt thereof.

International patent application No. WO 84/02131 published June 7, 1984 describes analogs of mevalonolactone having the structure

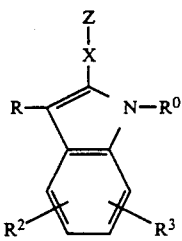

wherein: one of R and $R^0$ is

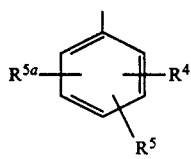

and the other is primary or secondary $C_{1-6}$ alkyl, $C_{3-6}$ cycloalkyl or phenyl-$(CH_2)_n$—;

X is —$(CH_2)_n$— or —CH=CH—;

n is 0, 1, 2 or 3;

Z is

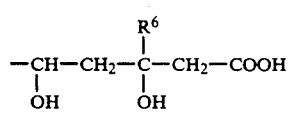

and $R^4$, $R^5$, $R^{5a}$ and $R^6$ represent various substituents.

International patent application No. WO 84/02903 published Aug. 2, 1984 describes mevalonolactone analogs having the structures

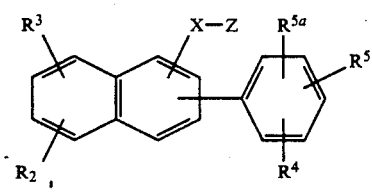   IA

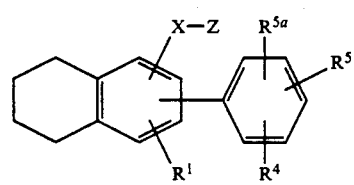   IB wherein

X is —$(CH_2)n$—,

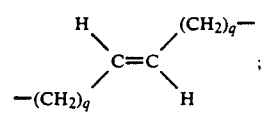

n=0, 1, 2, or 3 and both q's are 0 or one is 0 and the other is 1 and

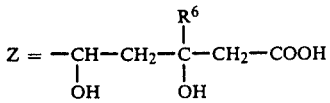

European patent application No. EP-142,146 published May 22, 1985 describes oxo- analogs of mevinolin-like antihypercholesterolemic agents having the structure

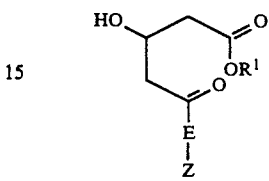

wherein

E is —$CH_2$—$CH_2$—, —CH=CH— or —$(CH_2)_3$—; and

Z is

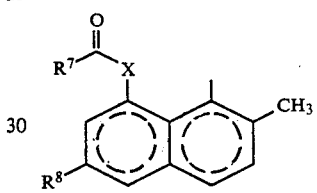

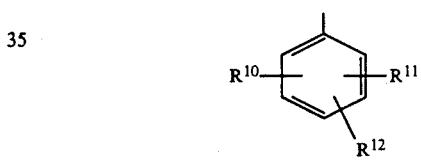

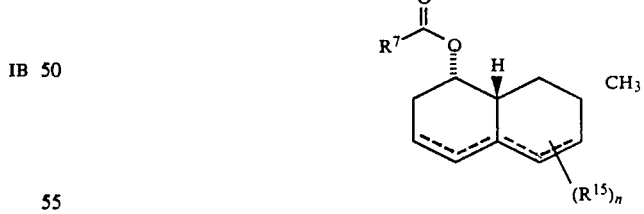

wherein the dotted lines represent possible double bonds there being 0, 1, or 2 double bonds.

In J. Med. Chem., 28, 347–358 (1985), G. E. Stokker, et al. report the preparation and testing of a series of 5-substituted 3,5-dihydroxypentanoic acids and their derivatives.

In J. Med. Chem., 29, 159–169 (1986), W. F. Hoffman, et al. describe the preparation and testing of a series of 7-(substituted aryl)-3,5-dihydroxy-6-heptenoic (heptanoic) acids and their lactone derivatives. One of the preferred compounds in the reported series has the structure

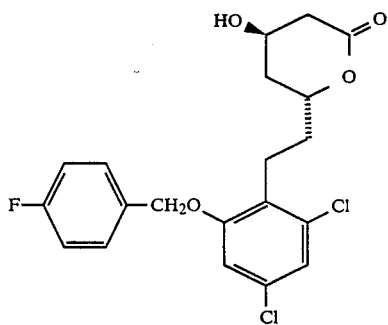

In J. Med. Chem., 29, 170–181 (1986), G. E. Stokker, et al. report the synthesis of a series of 7-[3,5-disubstituted (1,1'-biphenyl)-2-yl]-3,5-dihydroxy-6-heptenoic acids and their lactones. Two of the preferred compounds reported in this article have the structures

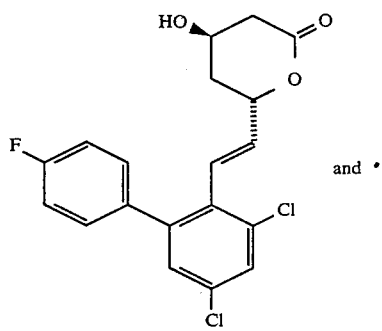

and

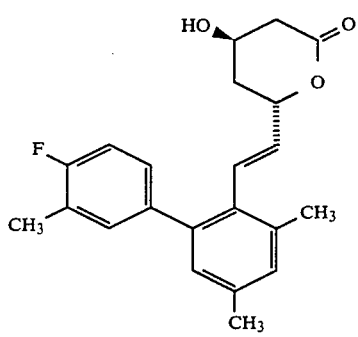

U.S. Pat. No. 4,613,610, issued Sept. 23, 1986 to J. R. Wareing describes pyrazole analogs of mevalonolactone and its derivatives useful for the treatment of hyperlipoproteinemia and atherosclerosis and having the general formula

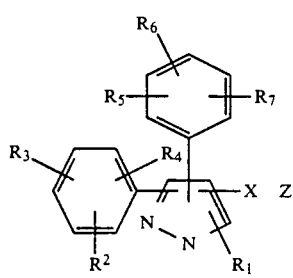

wherein X is —(CH$_2$)$_n$—, —CH=CH—, —CH=CH—CH$_2$— or —CH$_2$—CH=CH—; n is 0, 1, 2 or 3, and R$^1$, R$^2$, R$^3$, R$^4$, R$^5$, R$^6$, R$^7$ and 2 represent various substituents.

None of the cited patents and articles disclose or suggest the possibility of preparing the compounds of the present invention. The unique structural feature which incorporates a tetrazole moiety in the present compounds differs substantially from the cited art.

SUMMARY OF THE INVENTION

The present invention provides novel tetrazole intermediates having the formula

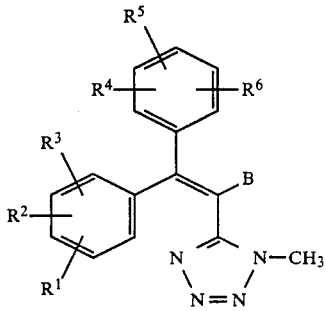

wherein R$^1$, R$^2$, R$^3$, R$^4$, R$^5$, R$^6$ and B are as defined below which ar useful for the preparation of inhibitors of the enzyme 3-hydroxy-3-methylglutaryl coenzyme A (HMG-CoA) reductase, which are useful in the treatment of hypercholesterolemia, hyperlipoproteinemia and atherosclerosis. The present invention also provides processes for the preparation of compounds of Formula I.

DESCRIPTION OF THE INVENTION

The present invention provides novel tetrazole intermediates which are useful for the preparation of antihypercholesterolemic agents, and which have the formula

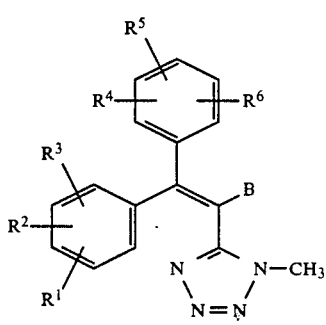

wherein
R$^1$ and R$^4$ each are independently hydrogen, halogen, C$_{1-4}$ alkyl, C$_{1-4}$ alkoxy or trifluoromethyl;
R$^2$, R$^3$, R$^5$ and R$^6$ each are independently hydrogen, halogen, C$_{1-4}$ alkyl or C$_{1-4}$ alkoxy;
B is hydrogen, C$_{1-6}$ alkoxycarbonyl, CH$_2$Y or CH$_2$Z;
Y is hydrogen, hydroxyl or X:
Z is

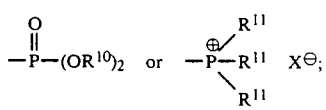

X is bromo, chloro or iodo;
$R^{10}$ is $C_{1-4}$ alkyl; and
$R^{11}$ is phenyl which is unsubstituted or substituted by one or two $C_{1-4}$ alkyl or chloro substituents.

This invention also provides Processes for the preparation of the compounds of Formula I and to processes for the preparation of antihypercholesterolemic agents of the formulae

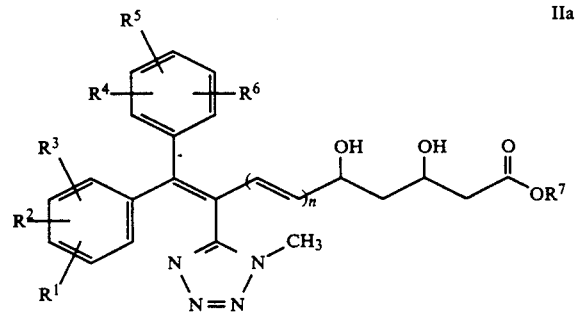

IIa

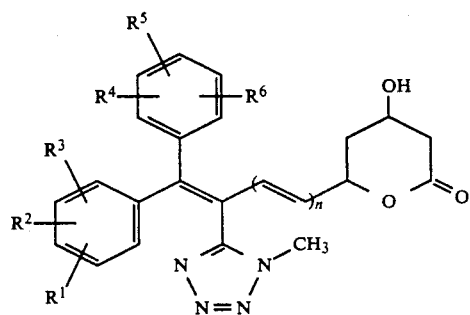

IIb wherein $R^1$ and $R^4$ each are independently hydrogen, halogen, $C_{1-4}$ alkyl, $C_{1-4}$ alkoxy, or trifluoromethyl; $R^2$, $R^3$, $R^5$ and $R^6$ each are independently hydrogen, halogen, $C_{1-4}$ alkyl or $C_{1-4}$ alkoxy; n is 0, 1 or 2; and $R^7$ is hydrogen, a hydrolyzable ester group or a cation to form a non-toxic pharmaceutically acceptable salt.

The terms "$C_{1-4}$ alkyl", "$C_{1-6}$ alkoxycarbonyl" and "$C_{1-4}$ alkoxy" as used herein and in the claims (unless the context indicates otherwise) mean unbranched or branched chain alkyl or alkoxy groups such as methyl, ethyl, propyl, isopropyl, butyl, isobutyl, t-butyl, amyl, hexyl, etc. Preferably, these groups contain from 1 to 4 carbon atoms and, most preferably, they contain 1 or 2 carbon atoms. Unless otherwise specified in the particular instance, the term "halogen" as used herein and in the claims is intended to include chlorine, fluorine, bromine and iodine while the term "halide" as used herein and in the claims is intended to include chloride bromide and iodide anion. The term "a cation to form a non-toxic pharmaceutically acceptable salt" as used herein and in the claims is intended to include non-toxic alkali metal salts such as sodium, potassium, calcium and magnesium, the ammonium salt and salts with non-toxic amines such as trialkylamines, dibenzylamine, pyridine, N-methylmorpholine, N-methylpiperidine and other amines which have been used to form salts of carboxylic acids. Unless otherwise specified, the term "a hydrolyzable ester group" as used herein and in the claims is intended to include an ester group which is physiologically acceptable and hydrolyzable under physiological conditions such as $C_{1-6}$ alkyl, phenylmethyl and pivaloyloxymethyl.

In the compounds of Formulae IIa and IIb, it is intended that all of the double bonds are in the trans configuration, i.e., (E), as indicated in the structural formulae used herein.

In the compounds of Formula I, $R^1$, $R^2$, $R^3$, $R^4$, $R^5$ and $R^6$, independently, are preferably hydrogen, halogen, $C_{1-4}$ alkyl or $C_{1-4}$ alkoxy. More preferably, $R^1$ and $R^4$ are hydrogen and $R^2$, $R^3$, $R^5$ and $R^6$, independently, are hydrogen, fluoro, chloro, methyl or methoxy, and most preferably, $R^1$ and $R^4$ are hydrogen and $R^2$, $R^3$, $R^5$ and $R^6$, independently, are hydrogen, fluoro, methyl or methoxy. It is preferred that B is hydrogen, ethoxycarbonyl, $CH_2Y$ in which Y is preferably hydrogen, hydroxyl, chloro or bromo, or $CH_2Z$ in which Z is preferably triphenylphosphonium bromide or $C_{1-2}$ alkyl phosphonate.

The antihypercholesterolemic compounds of Formulae IIa and IIb may be prepared by various procedures and preferably by employing the intermediates of the formula 5

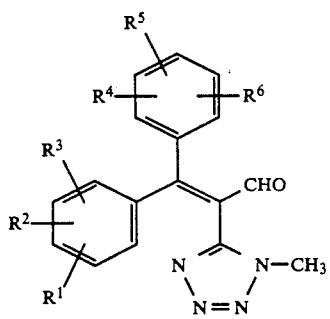

III wherein $R^1$, $R^2$, $R^3$, $R^5$ and $R^6$ are as defined previously. Thus, the present invention provides novel intermediates of the Formula I and improved processes for the preparation of compounds of the Formula III.

The compounds of Formula III may be prepared by various procedures, preferably starting from a compound of the Formula IV

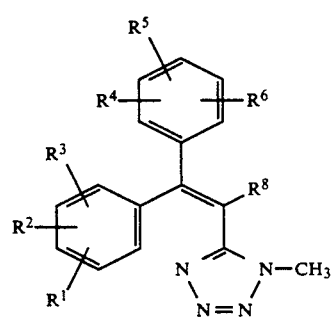

IV wherein $R^1$, $R^2$, $R^3$, $R^4$, $R^5$ and $R^6$ are as previously defined; and $R^8$ is hydrogen, $C_{1-6}$ alkoxycarbonyl or methyl.

The compounds of Formula IV may be prepared from the optionally substituted benzophenones of Formula V by alkylation with the appropriately 5-substituted 1-methyltetrazole of Formula VI followed by dehydration of the resulting tertiary alcohol of Formula VII, as shown in Reaction Scheme 1.

Reaction Scheme 1

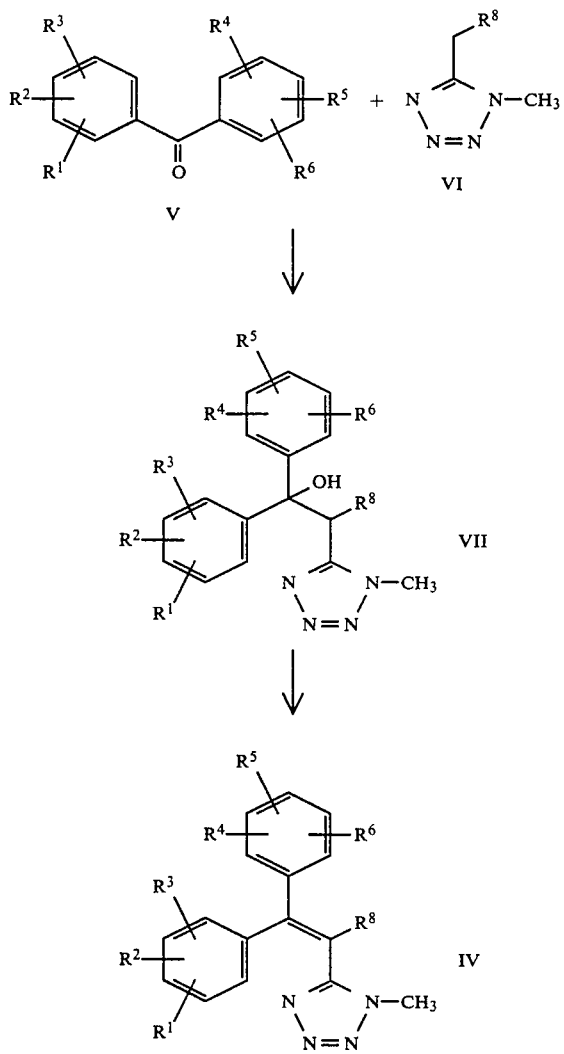

In Reaction Scheme 1, $R^1$, $R^2$, $R^3$, $R^4$, $R^5$, $R^6$, and $R^8$ are as previously defined. The optionally substituted benzophenones of the Formula V may be prepared by the general and well-known Friedel Crafts reaction of a substituted phenyl catalyzed by Lewis acids, e.g., with aluminum chloride in carbon tetrachloride at about 0° C. A large number of substituted benzophenones are known and their preparation are described in the art while many others are commercially available. For example, many of the starting materials of Formula V are described by G. Olah in *Friedel-Crafts and Related Reactions*, Vol. 3. part 1 and 2, Interscience publishers, New York, 1964 and references therein. The Friedel-Crafts reaction may produce a mixture of benzophenones and, if so produced, the mixture may be separated by conventional techniques known in the art.

The starting materials of Formula VI wherein $R^8$ is hydrogen is commercially available while the starting materials wherein $R^8$ is $C_{1-6}$ alkoxycarbonyl or methyl may be prepared by reacting 1,5-dimethyltetrazole with a strong base such as butyllithium at a temperature of about $-70°$ C. to about $0°$ C. and the resulting anion thereof is added to or treated with, preferably, ethyl chloroformate or methyl iodide, respectively, as described herein.

The appropriate 5-substituted 1-methyltetrazole of Formula VI may be treated with a strong base such as n-butyllithium at low temperatures of from about $-20°$ C. to about $-78°$ C, and preferably, from about $-40°$ C. to $-78$ an inert organic solvent, e.g., tetrahydrofuran, diethyl ether, 1,2-dimethoxyethane and the like. The resulting anion of Formula VI may then be treated with the desired benzophenone of Formula V to produce the corresponding tertiary alcohols of Formula VII.

The compounds of Formula IV may be prepared from the compounds of Formula VII by conventional dehydration procedures. The dehydration may be carried out by heating the alcohol of Formula VII in a suitable inert organic solvent, e.g., toluene, benzene or xylene, with a small amount of organic or mineral acid such as P-toluenesulfonic acid or sulfuric acid in the presence of a drying agent, e.g., $Na_2SO_4$, $MgSO_4$, molecular sieves, etc., or preferably, the water which is produced is azeotropically removed with a Dean-Stark trap or similar apparatus. Alternatively, the alcohol of Formula VII may simply be heated with potassium hydrogen sulfate at temperatures of about 190° C.

In the specific example wherein is ethoxycarbonyl, the reaction of ethyl 1-methyl-5-tetrazolylacetate with a benzophenone of Formula V may be conducted in the presence of titanium tetrachloride and carbon tetrachloride to directly produce, in one step, the corresponding olefin of Formula IV.

The preferred aldehydes of Formula III may be prepared by various procedures from the compounds of Formula IV depending on which $R^8$ substituent is employed in the procedure. Thus, it should be appreciated by those skilled in the art, that the compounds of Formula IV wherein $R^8$ is ethoxycarbonyl (Ia), hydrogen (Ic) or methyl (Id) may be converted to the aldehydes of Formula III, as shown in Reaction Scheme 2.

Reaction Scheme 2

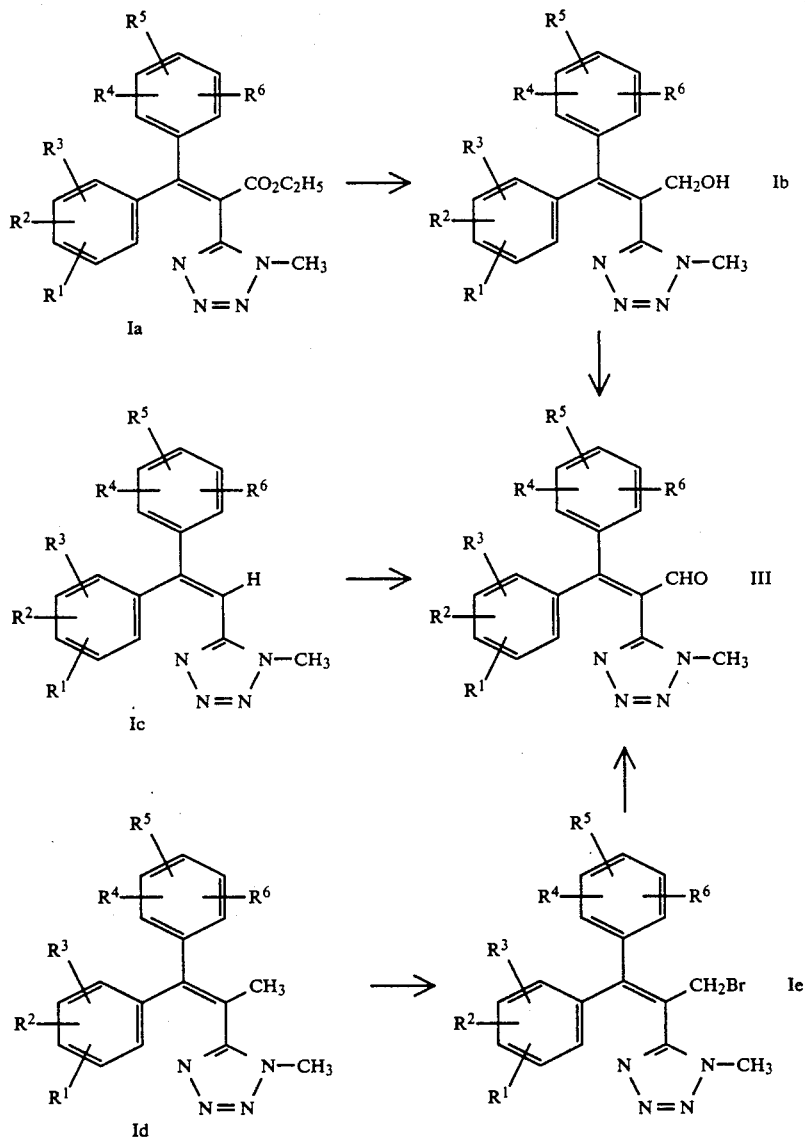

In reaction Scheme 2, $R^1$, $R^2$, $R^3$, $R^4$, $R^5$ and $R^6$ are as previously defined. The alcohols of Formula Ib may preferably be prepared in one step by reduction of the tetrazole ester of Formula Ia with reducing agents such as diisobutylaluminum hydride in a non-reducible inert solvent such as methylene chloride and tetrahydrofuran, at low tempertaures, and preferably at about $-78°$ C. The resulting allylic alcohols of Formula Ib may then be readily oxidized by conventional oxidizing agents such as pyridinium chlorochromate in a non-reactive solvent, preferably, methylene chloride at ambient temperature to produce the desired aldehyde of Formula III.

The compounds of Formula Ic may be converted directly to the aldehydes of Formula III by treating the anion of Formula Ic, which is produced in situ in an inert organic solvent, e.g., tetrahydrofuran or 1,2-dimethoxyethane with a strong base such as n-butyllithium with ethyl formate.

The compounds of Formula III may also be prepared from the compounds of Formula Id by first treating the compounds of Formula Id with N-bromosuccinimide in the presence of a catalyst such as azobis isobutyronitrile or benzoyl peroxide in carbon tetrachloride, and then reacting the resulting allylic bromide of Formula Ie with 2-nitropropane by the general procedure described herein and in Org. Syn. Coll. Vol. IV, 93Z. Alternatively, the allylic bromide of Formula Ie may be prepared from the alcohol of Formula Ib by treatment with carbon tetrabromide and triphenylphosphine.

The preferred compounds of Formula III may be converted to the preferred compounds of Formula IIa and IIb by the general procedures described herein and in U.S. patent Ser. No. 018,542 filed Feb. 25, 1987, now abandoned and in the corresponding continuation-in-part thereof U.S. patent application Ser. No. 151,513 filed 2/18/88 (concurrently) by John J. Wright and Sing-Yuen Sit, now U.S. Pat. No. 4,897,490. The use of the aldehydes of Formula III is illustrated in Reaction Scheme 3.

Reaction Scheme 3

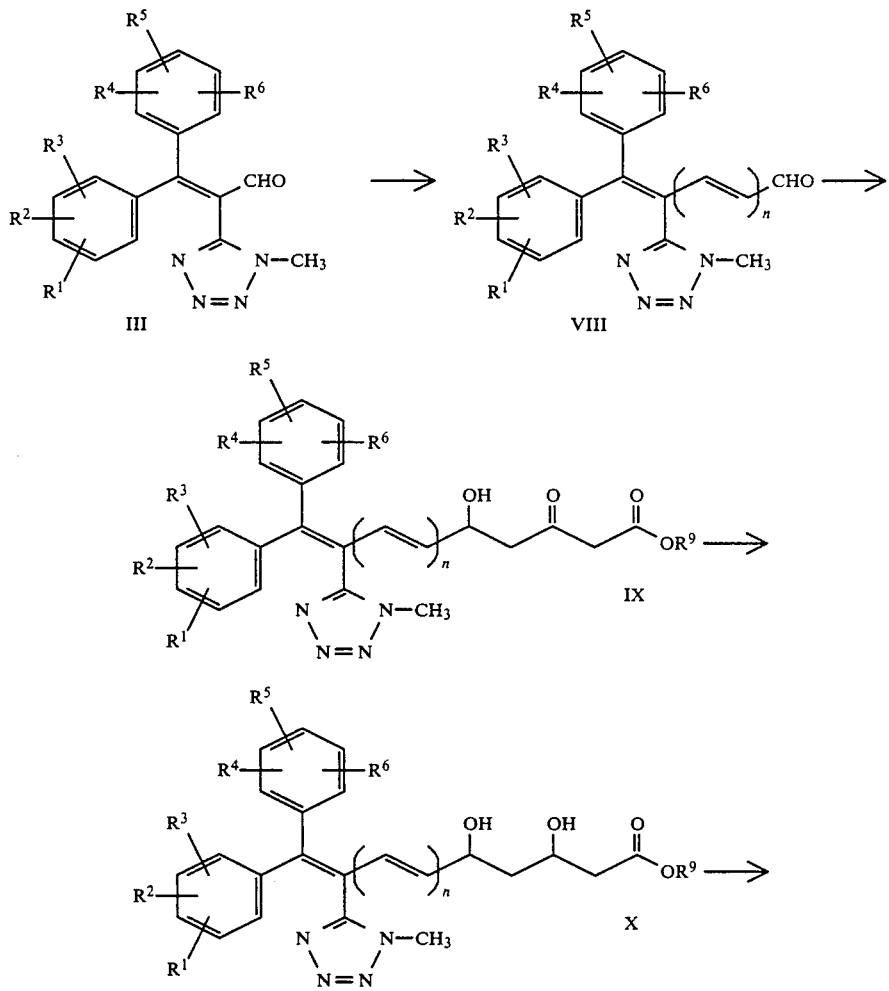

Compounds of the Formula IIa and IIb

In Reaction Scheme 3, $R^1$, $R^2$, $R^3$, $R^4$, $R^5$ and $R^6$ are as previously defined and R is a hydrolyzable ester group. In general, the aldehydes of Formula III may be converted to the diene aldehydes of Formula VIII wherein n=1 by reaction with about one equivalent of triphenylphosphoranylidene acetaldehyde in an inert organic solvent such as benzene, toluene, tetrahydrofuran, 1,2-dimethyoxyethane and the like. For convenience we prefer to conduct the reaction at reflux temperature. If it is desired, the diene aldehyde of Formula VIII wherein n=1 may be reacted with another equivalent of triphenylphosphoranylidene acetaldehyde to produce the triene aldehyde of Formula VIII wherein n=2.

The penultimate intermediate of Formula IX wherein $R^9$ is a hydrolyzable ester group may be prepared from the corresponding aldehyde of Formula VIII by reaction with the dianion of acetoacetate ester generated in situ, as described herein. The reaction may be conducted in an inert organic solvent such as tetrahydrofuran at low temperatures from −78° C. to about 0° C. and preferably from about −78° C. to −40° C. until the reaction is essentially complete.

The ketone ester of Formula IX may be reduced to the dihydroxy ester of Formula IIa by reduction of the ketone radical with reducing agents well-known in the art, e.g., sodium borohydride, sodium cyanoborohydride, zinc borohydride, disiamylborane, diborane, ammonia borane, t-butylamine borane, pyridine borane, lithium tri-s-butylborohydride or other similar reducing agents which will not reduce nor hydrolyze the carboxylic ester radical. Preferably, the reduction is carried out in a stereospecific manner by a two-step stereospecific reduction in order to maximize the production of the preferred erythro isomer of the compound of Formula IIa. The stereospecific reduction of a compound of Formula IX is carried out with trisubstitutedalkylboranes, preferably triethylborane, or alkoxydialkylboranes, preferably methoxydiethylborane or ethoxydiethylborane [*Tetrahedron Letters*, 28 155 (1987)] at a temperature of about −70° C. to about ambient temperature. The complex which is produced is then reduced with sodium borohydride at a temperature of about −50° C. to about −78° C. in an inert organic solvent such as tetrahydrofuran, diethyl ether and 1,2-dimethoxyethane, preferably, tetrahydrofuran. The reduction is then completed by the addition of methanol. The resulting compound of Formula X may then be converted to the compounds of general Formulae IIa and IIb in a conventional manner well-known to those skilled in the art.

In an alternate procedure for the preparation of compounds of the Formulae IIa and IIb there is also provided intermediates of the Formulae If and Ig, as shown in Reaction Scheme 4.

Reaction Scheme 4

Reaction Scheme 5

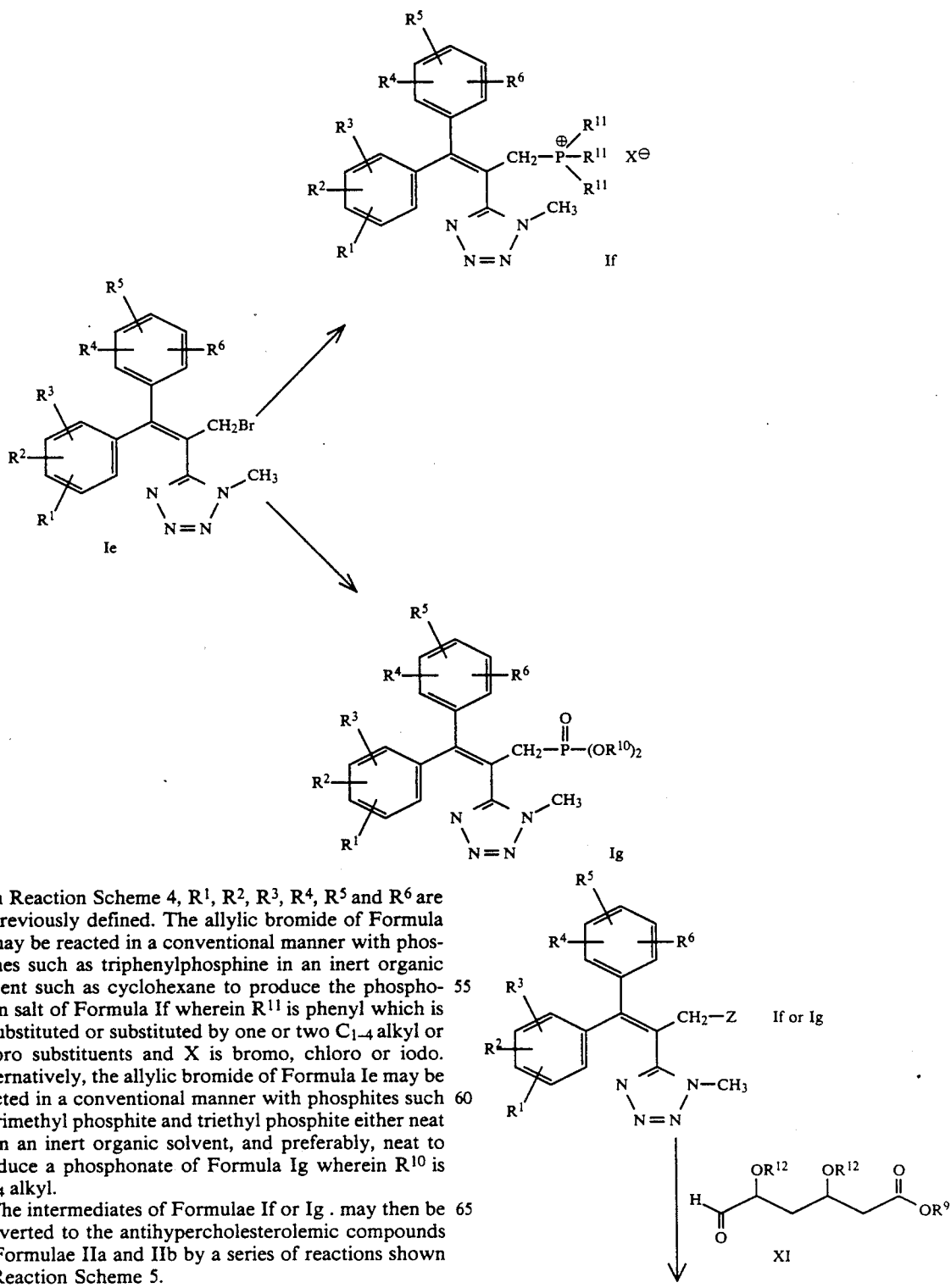

In Reaction Scheme 4, $R^1$, $R^2$, $R^3$, $R^4$, $R^5$ and $R^6$ are as previously defined. The allylic bromide of Formula Ie may be reacted in a conventional manner with phosphines such as triphenylphosphine in an inert organic solvent such as cyclohexane to produce the phosphonium salt of Formula If wherein $R^{11}$ is phenyl which is unsubstituted or substituted by one or two $C_{1-4}$ alkyl or chloro substituents and X is bromo, chloro or iodo. Alternatively, the allylic bromide of Formula Ie may be reacted in a conventional manner with phosphites such as trimethyl phosphite and triethyl phosphite either neat or in an inert organic solvent, and preferably, neat to produce a phosphonate of Formula Ig wherein $R^{10}$ is $C_{1-4}$ alkyl.

The intermediates of Formulae If or Ig . may then be converted to the antihypercholesterolemic compounds of Formulae IIa and IIb by a series of reactions shown in Reaction Scheme 5.

-continued
Reaction Scheme 5

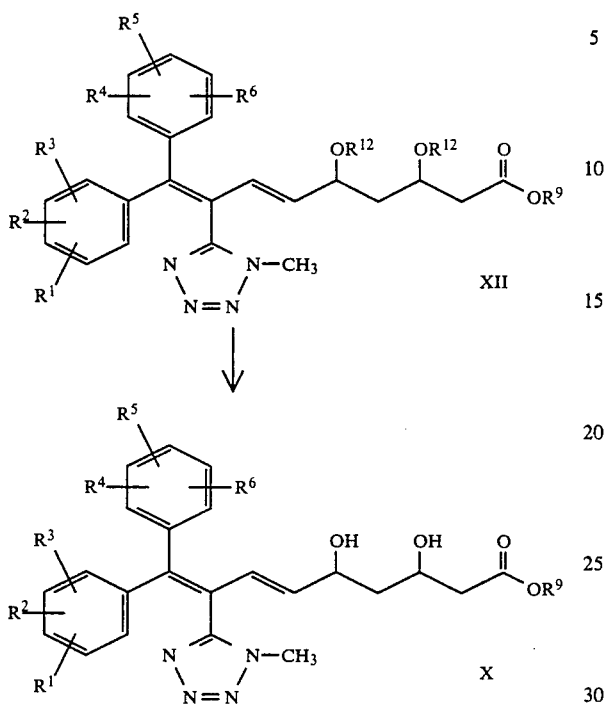

In Reaction Scheme 5, $R^1$, $R^3$, $R^4$, $R^5$, and $R^6$ are as previously defined, $R^9$ is a hydrolyzable ester group $R^{12}$ is t-butyldiphenylsilyl and Z is

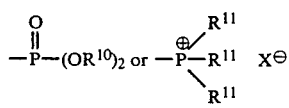

in which $R^{10}$ is $C_{1-4}$ alkyl, $R^{11}$ is phenyl which is unsubstituted or substituted by one or two $C_{1-4}$ alkyl or chloro substituents and X is bromo, chloro or iodo. The phosphonium salt of Formula If or the phosphonate of Formula Ig may be reacted with the silyl protected aldehyde of Formula XI which is itself prepared by the procedures described in Tetrahedron Letters, 25. 2435 (1984) and also in U.S. Pat. No. 4,571,428 to produce the silyl protected compound of Formula XII. The reaction may be conducted in an inert organic solvent such as tetrahydrofuran or N,N-dimethylformamide in the presence of a strong base, for example, lithium diisopropylamide, potassium t-butoxide and n-butyllithium at a temperature of about −78° C. to about 0° C. The compound of Formula XII may then be desilylated by well-known procedures such as 48% hydrofluoric acid and preferably, with tetrabutylammonium fluoride in an inert organic solvent such as tetrahydrofuran and acetonitrile in the presence of a small amount of organic acid to produce the erythro compounds of Formula X. The resulting compound of Formula X may then be converted to the compounds of general Formulae IIa and IIb in a conventional manner well-known to those skilled in the art.

In a preferred embodiment of the invention the compounds of Formula I have the structure

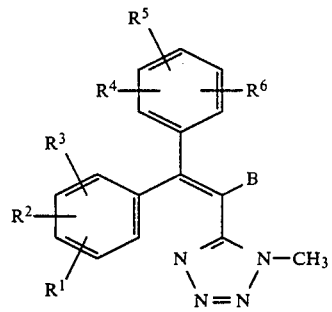

wherein $R^1$, $R^2$, $R^3$, $R^4$, $R^5$ and $R^6$ each are independently hydrogen, fluoro, methyl or methoxy; and B is hydrogen or $C_{1-6}$ alkoxycarbonyl.

In another preferred embodiment of the invention the compound of Formula I have the structure

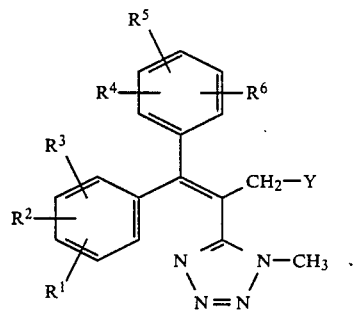

wherein $R^1$, $R^2$, $R^3$, $R^4$, $R^5$ and $R^6$ each are independently hydrogen, fluoro, methyl or methoxy; Y is hydrogen, hydroxyl or X; and X is bromo, chloro or iodo.

In still another preferred embodiment of the invention the compounds of Formula I have the structure

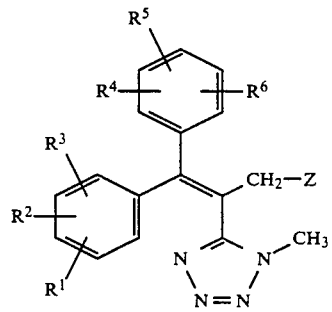

wherein $R^1$, $R^2$, $R^3$, $R^4$, $R^5$ and $R^6$ each are independently hydrogen, fluoro, methyl or methoxy and Z is

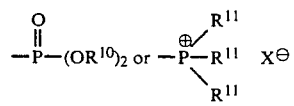

in which $R^{10}$ is methyl or ethyl; phenyl; and X is bromo.

The compounds of Formulae IIa and IIb are competitive inhibitors of the enzyme 3-hydroxy-3-methylglutaryl coenzyme A (HMG-CoA) reductase, the rate limiting enzyme in cholesterol biosynthesis, and therefore, are selective suppressors of cholesterol biosynthesis in animals, including man. Consequently, they are useful in the treatment of hypercholesterolemia, hyperlipoproteinemia and atherosclerosis. The biological activity of the compounds of Formulae IIa and IIb may be demonstrated by the inhibition of cholesterol biosynthesis in rats. In Vivo Acute Cholesterol Biosynthesis Inhibition in Rats Male Wistar rats (160-200 g, housed 2 per cage) were maintained on normal diet (Purina Rat Chow and water, ad libitum) for at least 7 days on a reversed lighting schedule (7:00 a.m. to 5:00 p.m. dark). Food was removed 15 hours prior to dosing. Compounds were administered at 8:00 a.m. by intragastric intubation using 0.5-1.0 mL of water or propylene glycol solutions of sodium salts, lactones, or esters of the test compounds. Controls received equal volumes of the vehicle.

Thirty minutes after receiving the test substances, rats were injected intraperitoneally with 0.9 mL of 0.9% NaCl containing approximately 120 uCi per kg body weight of sodium [1-$^{14}$C]acetate (1-3 mCi/mmol). After a 60 minute incorporation period, rats were sacrificed and liver and blood samples were obtained. Aliquots of plasma (1.0 mL) obtained by centrifugation of heparin EDTA-treated blood, and aliquots of liver homogenates (equivalent to 0.50 g liver wet weight) were taken for determination of radiolabeled 3-hydroxy sterols. Sterol isolation for the liver samples followed the method of Kates in Techniques in Lipidology, (M. Kates, ed.) pp. 349, 360-363, North Holland Publ Co., Amsterdam, 1972 while the plasma samples were directly saponified followed by isolation of the digitonin-precipitable sterols. $^{14}$C-labelled sterols were quantified by liquid scintillation counting (efficiency corrected). Mean percent inhibition of $^{14}$C incorporated into liver and into plasma cholesterol was calculated for groups of treated animals and compared to mean values for controls conducted simultaneously.

Therefore, the above test provides information on the ability of test substances to suppress the de novo biosynthesis of cholesterol in vivo in rats with oral dosing. For example, using the above test, the compound of Example 9 yielded a 50% Inhibitory Dose ($ED_{50}$) for both plasma and liver cholesterol, comparable to values obtained for mevinolin (lovastatin) using a similar procedure [Alberts, et al., *Proc. Natl. Acad Sci.*, 77, 3957-3961 (1980)].

DESCRIPTION OF THE SPECIFIC EMBODIMENTS

In the following examples, all temperatures are given in degrees Centigrade. Melting points were recorded on a Thomas-Hoover capillary melting point apparatus and boiling points were measured at specific pressures (mm Hg) and both temperatures are uncorrected. Proton magnetic resonance ($^1$H NMR) spectra were recorded on a Bruker AM 300, Bruker WM 360 or Varian T-60 CW spectrometer. All spectra were determined in CDCl$_3$, DMSO-d$_6$ or D$_2$O unless otherwise indicated and chemical shifts are reported in $\delta$ units downfield from the internal standard tetramethylsilane (TMS) and interproton coupling constants are reported in Hertz (Hz). Splitting patterns are designated as follows: s, singlet; d, doublet, t, triplet;, q, quartet; m, multiplet; br, broad peak; and dd, doublet of doublet. Carbon-13 nuclear magnetic resonance ($^{13}$C NMR) spectra were recorded on a Bruker AM 300 or Bruker WM 360 spectrometer and were broad band proton decoupled. All spectra were determined in CDCl$_3$. DMSO-d$_6$ or D$_2$O unless otherwise indicated with internal deuterium lock and chemical shifts are reported in $\delta$ units downfield from tetramethylsilane. Infrared (IR) spectra were determined on a Nicolet MX-1 FT spectrometer from 4000 cm$^{-1}$, calibrated to 1601 cm$^{-1}$ absorption of a polystyrene film and are reported in reciprocal centimeters (cm$^{-1}$). Relative intensities are indicated as follows: s (strong), m (medium) and w (weak).

Gas chromatography-mass spectra (GC-MS) were determined on a Finnigan 4500 Gas chromatography - quadruple mass spectrometer at ionization potential of 70 eV. Mass spectra were also recorded on a Kratos MS-50 instrument utilizing the fast atom bombardment (FAB) technique The mass data are expressed in the format: parent ion (M+) or protonated ion (M+H)+.

Analytical thin-layer chromatography (TLC) was carried out on precoated silica gel plates (60F-Z54) and visualized using UV light, iodine vapors and/or staining with one of the following reagents: (a) methanolic phosphomolybdic acid (2%) and heating; (b) reagent (a) followed by 2% cobalt sulphate in 5M H and heating. Column chromatography, also referred to as flash column chromatography, was performed in a glass column using finely divided silica gel (32-63 $\mu$m on silica gel-H) and pressures somewhat above atmospheric pressure with the indicated solvents. All evaporations of solvents were performed under reduced pressure. As used herein, the term hexanes is a mixture of isomeric C$_6$ hydrocarbons as specified by the American Chemical Society, and the term "inert" atmosphere is an argon or nitrogen atmosphere unless otherwise indicated.

EXAMPLE 1

Ethyl 2-cyano-3,3 bis(4-fluorophenyl)-2 propenoate

A mixture of 20.0 g (92 mmoles) of 4,4'-difluorobenzobenzophenone 11.0 g (97 mmoles) of ethyl cyanoacetate in a mixed solvent of 100 mL of dry benzene and 20 mL of glacial acetic acid containing a catalytic amount of $\beta$-alanine (0.9 g) was refluxed with separation of water using a Dean-Stark water trap. Separation of water was rapid during the first 2 hours (0.4 mL aqueous layer collected) but slower afterward. Azeotropic distillation was continued for a period of 14 days. Analytical TLC eluted with 10% EtOAc in hexanes (v/v) (Merck plate, 0.Z5 mm Silica gel-F) showed two spots at $R_f$=0.2 (desired product) and at $R_f$=0.45 (4,4'-difluorobenzophenone starting material). Crude reaction mixture was washed with water (40 mL $\times$2), and the combined aqueous washes were extracted with EtOAc (150 mL $\times$2). The organic layers were combined, dried over MgSO$_4$ and concentrated under reduced pressure to crystallize the product as pale cubic crystals. The crude product was collected, washed with 1:1 EtOAc in hexanes (v/v) then recrystallized from 8:1 (hexanes:ethyl acetate v/v) to give 16.2 g (56.3%) of analytical pure title compound; m.p.=114°-116° C.

IR (KBr) $v_{max}$; 3000 (s), 2225 (s), 1931 (vs), (1605 (s), 1513 (s), 1250 (s), 844 (s) cm$^{-1}$;

$^1$H NMR (CDCl$_3$) $\delta$: 1.19 (3H, t, J=7.1 Hz), 4.18 (2H, q, J=7.1 Hz), 7.08-7.15 (6H, m), 7.40-7.42 (2H, m);

$^{13}$C NMR (CDCl$_3$) $\delta$: 13.75, 62.27, 104.05, 116.69, 115.53 (d, $^2J_{C-F}$=22.7 Hz), 115.88 (d, $^2J_{C-F}$=22.7 Hz), 131.64 (d, $^3J_{C-F}$=9.1 Hz), 132.66 (d, $^3J_{C-F}$=9.1 Hz), 134.25, 134,31, 134.36, 164.01 (d, $^1J_{C-F}$=252.9 Hz). 164.52 (d, $^1J_{C-F}$=254.0 Hz). 166.65 ppm.

Anal. Calcd. for C$_{18}$H$_{13}$NO$_2$F$_2$: C, 69.01; H, 4.15; N, 4.47. Found: C, 68,91; H, 4.15; N, 4.62.

EXAMPLE 2

Ethyl 3,3-bis(4-fluorophenyl)-2-(1H-tetrazol-5-yl)-2-propenoate

A dry 50 mL round bottom flask was charged with 5.0 g (16.0 mmoles) of ethyl 2-cyano 3,3-bis(4-fluorophenyl)-2-propenoate followed by 8.0 g (24.1 mmoles) of azidotributylstannane [prepared by the procedure described in Rev. Trav. Chim. 81, 202–5 (1962)]and 2.0 mL of reagent grade toluene. The heterogenous mixture was stirred and heated to reflux (110° C.) in an oil bath behind a safety shield. The solid starting material dissolved gradually forming a pale yellowish thick syrup and the homogenous mixture was stirred and refluxed for 20 hours. Analytical TLC eluted with 20% MeOH in CHCl$_3$ (v/v) showed the product at R$_f$=0.26 (streak). The crude reaction mixture was diluted with an equal volume of diethyl ether and was poured into a vigorously stirring saturated aqueous solution of KF (200 mL containing 2 mL of 48% HBF$_4$). A voluminous precipitate (Bu$_3$SnF) was observed soon after mixing and the hydrolysis was allowed to proceed for 16 hours. The suspension was filtered and the filtrate was extracted with EtOAc (100 mL ×2). The organic layers were combined, dried over MgSO$_4$ and concentrated under reduced pressure. The title compound crystallized from the concentrate yielding 4.54 g (77%) of white analytical pure material; m.p.=159°–161° C.

IR (KBr) $\mu_{max}$: 3438 (br), 1713 (vs), 1600 (s), 1510 (s). 1238 (s). 841 (s) cm$^{-1}$.

$^1$H NMR (CDCl$_3$) δ: 0.92 (3H, t, J=7.6 Hz), 3.98 (2H, q, J=7.6 Hz), 7.3–6.7 (8H, m). 10 (1H, v.br.);

$^{13}$C NMR (CDCl$_3$) δ: 166.52, 163.54 (d, $^1J_{C-F}$=250.7 Hz), 163.46, (d, $^1J_{C-F}$=2.62.7 Hz), 157.14. 136.40, 134.74, 131.71 (d, $^2J_{C-F}$67.2 Hz), 131.59 (d, $^2J_{C-F}$=66.4 Hz), 115.75 (d, $^3J_{C-F}$=18.9 Hz), 115.45 (d, $^3J_{C-F}$=18.1 Hz) 62.11, 13.47 ppm.

Anal. Calcd. for C$_{18}$H$_{14}$F$_2$N$_4$O$_2$: C, 60.27; H, 4.06; N, 15.50. Found: C, 60.67; H, 3.96; N, 15.72.

EXAMPLE 3

Ethyl 3,3-bis(4-fluorophenyl)-2-(1-methyl-1H-tetrazol-5-yl)-2-propenoate

To a solution of 0.5 g (1.40 mmoles) of ethyl 3,3-bis(4-fluorophenyl)-2-(1H-tetrazol-5-yl)-2-propenoate in 100 mL of dry benzene at 45° C. under argon was added sodium hydride 100 mg (60% in mineral oil 2.5 mmoles) in one single portion. The greyish suspension was stirred at 45° for 30 minutes then 1 mL (16.1 mmoles) of methyl iodide was added, and the flask was sealed with a rubber stopper. Alkylation was allowed to proceed at 40°–45 C. for a total of four days. Analytical TLC eluted twice with 20% EtOAc in hexanes showed only two isomeric products at R$_f$=0.16 (major isomer) and R$_f$=0.22 (minor isomer) The crude reaction mixture was washed with an equal volume of water and the aqueous phase was back extracted once with 50 mL of diethyl ether. The organic layers were combined, dried over MgSO$_4$ and concentrated under reduced pressure to give crude product.

The crude product mixture which was prepared as described above (5.0 g) was taken into 20 mL of hot ethyl acetate to which was added 40 mL of hot hexanes. The clear solution was allowed to cool slowly to room temperature to give 2.16 % (52%) of the title compound as colorless large needles; m.p.=144°–145° C.

IR (KBr) $\nu_{max}$: 1713 (vs), 1600 (s), 1513 (s), 1325 (s), 1163 (s), 838 (s) cm$^{-1}$;

$^1$H NMR (CDCl$_3$) δ: 7.4–6.8 (8H, m), 4.06 (2H, q, J=7.1 Hz) 3.68 (3H, s), 1.00 (3H, t, J=7.1 Hz);

$^{13}$C NMR (CDCl$_3$)δ: 165.44, 163.6 (d, $^1J_{C-F}$=250.7 Hz), 163.4 (d, $^1J_{C-F}$=252.9 Hz) 156.85, 152.37, 135.88, 131.32 (d, $^3J_{C-F}$=8.3 Hz), 115.94 (d, $^8J_{C-F}$=21.9 Hz), 115.64 (d, $^2J_{C-F}$=22.7 Hz). 61.84, 33.76, 13.59 ppm;

Anal. Calcd. for C$_{19}$H$_{16}$F$_2$N$_4$O$_2$: C, 61.62; H, 4.35; N, 15.13 Found: C, 61.63; H, 4.45; N, 15.21.

EXAMPLE 4

3,3-Bis(4-fluorophenyl)-2-(1-methyl-1H-tetrazol-5-yl)-2-propenoic acid

To a solution of ethyl 3,3-bis(4-fluorophenyl-2-(1-methyl-1H-tetrazol-5-yl) 2-propenoate 4.0 g (10.8 mmoles) in a mixture containing 20 mL of methanol and 20 mL tetrahydrofuran at 0° C. (ice-water bath) was added a solution of 3 Molar lithium hydroxide in H$_2$O (9 mL). Saponification reaction was allowed to proceed overnight (ca. 16 hours) forming a clear homogeneous solution. Analytical TLC eluted twice with 30% ethyl acetate in hexanes (v/v) showed the desired product at the origin. Crude reaction mixture was made acidic by adding 10 mL of 3 Molar HCl solution and the organic material was extracted twice into ethyl acetate (20 mL×2). Organic layers were combined, dried over MgSO$_4$ and concentrated under reduced pressure to give the product as a pale yellow solid. Recrystallization from EtOAc-hexanes mixture (1:9; v/v) yielded 3.8 g (100%) of the title compound; m.p.=205°–206° C.

IR (KBr) $\nu_{max}$: 3438 (br), 2900 (br), 1725 (s), (s), 1600 (s), 1501 (s), 1231 (vs), 1156 (s), 850 (s) cm$^{-1}$; $^1$H NMR (CDCl$_3$) δ: 7.9–6.4 (8H, m), 3.68 (3H, s);

$^{13}$C NMR (CDCl$_3$) δ: 166.57, 163.3 d. $^1J_{C-F}$=249.9 Hz), 163.03 (d, $^1J_{C-F}$=250 Hz) 155.68, 152.61, 135.58, 134.74, 131.75 (d, $^3J_{C-F}$=8.3 Hz), 131.28 (d, $^3J_{C-F}$=9.1 Hz) 117. 115.7 (d, $^2J_{C-F}$=22.6 Hz), 115.4 (d. $^2J_{C-F}$=22.6 Hz). 33.6 ppm;

Anal. Calcd. for C$_{17}$H$_{12}$F$_2$N$_4$O$_2$: C, 59.05; H, 3.53; N. 16.37. Found C, 59.54; H. 3.58; N. 16.27.

EXAMPLE 5

3,3-Bis(4-fluorophenyl)-2-(1-methyl-1H-tetrazol-5-yl)-2-propenal

A.
3,3-Bis(4-fluorophenyl)-2-(1-methyl-1H-tetrazol-5-yl)-2-propenoyl chloride To a solution of dry (0.1 mmHg at 80° C.) 3,3.bis(4-fluorophenyl)-2-(1-methyl-1H-tetrazol-5-yl)-2-propenoic acid 3.8 g (11.0 mmoles) in 20 mL of dry methylene chloride was added 4 mL (46.0 mmoles) of purified oxalyl chloride (redistilled over CaH$_2$) in one single portion. The reaction mixture was warmed gradually to reflux temperature for two hours. The mixture was evaporated under reduced pressure to remove volatile solvent then excess oxalyl chloride was removed under vacuum (20 mmHg) at ambient temperature for 2 hours and under high vacuum (0.1 mmHg) at 50° C. for 16 hours to give the title compound.

B. 3,3-Bis(4-fluorophenyl)-2-(1-methyl-1H-tetrazol-5-yl)-2-propenol

The acyl chloride prepared in step A was dissolved into 150 mL of tetrahydrofuran and was chilled to −78° C. under argon. To this pale brownish solution at −78° C. was added 8.0 mL lithium aluminum hydride in THF solutions (1.0 Molar). Analytical TLC after 15 minutes showed only one mobile spot at $R_f=0.23$ (50% EtOAc in hexanes v/v). The crude reaction mixture was diluted with 2M $H_2SO_4$ (20 ml). The aqueous layer was extracted with ethyl acetate (40 mL×2). Organic layers were combined, dried over $MgSO_4$ and concentrated under reduced pressure to give 3.64 g (100%) of the title compound. The crude allylic alcohol was used immediately in the next step without further purification. MS (CI): m/e=328 for $(M+H)^+$;

IR (KBr) $\nu_{max}$: 3388 (v.br). 1600 (s), 150 (s), 1225 (s), 1156 (s), 838 (s), 750 (s), cm$^{-1}$;

$^1$H NMR (CDCl$_3$) δ: 7.5–6.9 (8H, m), 4.52 (2H, br), 3.42 (3H, s), 3.75 (1H, br, D$_2$O exchangeable);

$^1$H NMR (DMSO-d$_6$) δ: 7.5–6.9 (8H, m), 5.23 (1H, t, J=5.5 Hz), 4.27, (2H, d, J=5.5 Hz), 354 (3H, s) ppm; C. 3,3-Bis(4-fluorophenyl)-2-(1-methyl-1H-tetrazol-5-yl)-2-propenal To a vigorously stirred solution of the crude allylic alcohol 3.64 g [prepared in Step B] in 40 mL of methylene chloride at room temperature was added 2.6 g (12.0 mmoles) of pyridinium chlorochromate in one single portion. Analytical TLC immediately afterward showed about 50% of product at $R_f=0.34$ along with the starting material at $R_f=0.14$ (eluted with 50% EtOAc:Hexanes v/v). The oxidation was allowed to proceed at room temperature for a total of 16 hours, during which all the starting material was consumed and TLC showed only product. The crude reaction suspension was filtered through a bed of silica gel, washed with one liter of 10% (v/v) ethyl acetate in hexanes and one liter of 20% (v/v) ethyl acetate in hexanes. The desired product crystallized upon concentration under reduced pressure to give 2.7 g (74%) of the title compound; m.p.=141°–142° C. MS (CI): m/e=326 for $(M+H)^+$;

IR (KBr) $\nu_{max}$ 3075 (m), 2875(m), 1675 (s), 1600 (s), 1501 (s), 1238 (s), 1156 (s), 850 (s), 750 (s), cm$^{-1}$;

$^1$H NMR (CDCl$_3$) δ: 9.63 (1H, s), 9.5–6.9 (8H, m), 3.74 (3H, s);

$^{13}$C NMR (CDCl$_3$) δ: 188.92, 165.44, 164.68 (d, $^1J_{C-F}$=254.4 Hz), 164.10 (d, $^1J_{C-F}$ Hz), 151.34, 134.31, 133.77 (d, $^3J_{C-F}$=8.3 Hz), 132.69, 132.23 (d, $^3J_{C-F}$=7.5 Hz) 123.70, 116.26 (d, $^2J_{C-F}$=21.9 Hz), 116.18 (d, $^2J_{C-F}$=22.7 Hz), 34.10 ppm;

Anal Calcd. for $C_{17}H_{12}F_2N_4O$: C, 62.58; H, 3.71; N, 17.17. Found: C, 62.41; H, 3.85; N, 16.98.

EXAMPLE 6

5.5-Bis(4-fluorophenyl)-4-(1-methyl-1H-tetrazol.5-yl)-2,4-pentadienal

A solution of 3,3-bis(4-fluorophenyl).2-(1-methyl-1H-tetrazol-5-yl)propenal (1.0 g, 3.07 mmoles) and triphenylphosphoranylidene acetaldehyde (0.93 g, 3.07 mmoles) in benzene was heated at reflux for 1 hour. The benzene was removed in vacuo and the residue was purified by column chromatography on silica gel eluting with 15% (v/v) ethyl acetate in hexane to give 0.7 g of the title compound; m.p.=156°–157.5° C.

Anal. Calcd. for $C_{19}H_{14}F_2N_4O$: C, 64.77; H, 4.01; N, 15.91. Found: C, 65.13; H, 4.05; N, 15.71.

EXAMPLE 7

Ethyl 9,9-bis(4-fluorophenyl)-5-hydroxy-8-(1-methyl-1H-tetrazol-5-yl)-3-oxo-6,8-nonadienoate To a chilled suspension (0° C., ice-water bath) of NaH (0.64 g, 16.0 mmoles) (60% in mineral oil) in 20 mL of dry tetrahydrofuran under argon was added ethyl acetoacetate 2.04 mL (16.0 mmoles) in 4 equal portions. The homogeneous clear solution was stirred at 0° C. for 30 minutes followed by the dropwise addition of 6.4 mL of 2.5 Molar n-BuLi (16.0 mmoles) over a period of 15 minutes. The orange dianion solution was stirred at 0° C. for an additional hour. The ice-water bath was replaced by an acetone-dry ice bath at −78° C. and the dianion was transferred via a cannula into a tetrahydrofuran (20 mL) solution containing 5,5-bis(4-fluorophenyl)-4-(1methyl-1H-tetrazol-5-yl)-2,4-pentadienal (2.82 g, 8.01 mmoles) Analytical TLC showed the major desired product at $R_f=0.15$ 150% EtOAc in hexanes) and a minor product at $R_f=0.2$. The crude reaction mixture was diluted with 40 mL of 1N HCl and the aqueous layer was extracted with ethyl acetate (50 mL×2). The organic layers were combined, dried over MgSO$_4$ and concentrated under reduced pressure. The desired product was purified by flash silica gel column chromatography eluted with 20% EtOAc in hexanes (v/v) to give 2.26 g (58.5%) of the title compound. MS (CI): m/e =483 for $(M+H)^+$.

IR (KBr) $\nu_{max}$; 3450 (v.br), 1738 (s). 1725 (s), 1606 (s), 1513 (vs), 1225 (s), 1163 (s), 844 (s) cm$^{-1}$;

$^1$H NMR (CDCl$_3$) δ: 7.4–6.8 (8H, m), 6.72 (1H, d, J=15.6 Hz), 4.63 (1H. m), 4.17 (2H, q, J=7.1 Hz), 4.13 (1H, m), 3.60 (3H, s), 3.52 (1H, d, J=3.9 Hz, D$_2$O exchangeable), 3.47 (2H, s), 2.74 (2H, d, J=6.0 Hz), 1.26 (3H, t, J=7.1 Hz) ppm;

$^{13}$C NMR (CDCl$_3$) δ: 164.21, 135.98, 132.34 (d, $^3J_{C-F}$=8.3 Hz), 131.45 (d, $^3J_{C-F}$=9.1 Hz), 115.74 (d, $^2J_{C-F}$=21.9 Hz), 115.74 (d, $^2J_{C-F}$=21.1 Hz), 100.86, 67.61, 61.58, 49.85, 49.07, 33.56. 14.10 ppm.

EXAMPLE 8

Ethyl (±)-erythro-9,9-bis(4-fluorophenyl) 3.5-dihydroxy8-(1-methyl-1H-tetrazol-5-Yl)-6,8-nonadienoate To a solution of ethyl 9,9-bis(4-fluorophenyl)5-hydroxy-8-(1-methyl-1H-tetrazol-5-yl)-3-oxo-6,8-nonadienoate (2.19 g, 4.53 mmoles) (dried under high vacuum at 30° C. for 48 hours) in 40 mL of anhydrous tetrahydrofuran at 0° C. (ice-water bath) under argon was added triethyl borane solution in tetrahydrofuran (4.8 mL, 4.8 mmoles) in one single portion. The mixture was stirred under argon for a total of one hour. The cooling ice-water bath was replaced with an acetone-dry ice bath and to the reaction mixture was added NaBH$_4$ (0.Z0 g, 5.3 mmoles) in one portion. The reaction suspension was stirred at −78° C. for two hours forming a clear homogeneous pale yellow solution. The crude reaction mixture was diluted with 40 mL of 1N HCl followed by extractions with EtOAc (40 mL×2). The organic layers were combined, dried over MgSO$_4$ and concentrated under reduced pressure to give the product as a thick syrup, it was further diluted with 300 mL of methanol and the solution was allowed to stand at room temperature for 16 hours before evaporation under reduced pressure. The crude product was purified by flash silica gel column chromatography using 2 liters of 30% EtOAc in hexanes as the eluting solvent. The appropriate fractions were collected and evaporated to give 1.48 % (68%) of the title compound. MS (CI): m/e=485 for (M+H)+;

IR (KBr) $\mu_{max}$: 3438 (s), 1734 (s), 1600 (s), 1513 (s), 1225 (s), 1163 (s), 844 (s), cm$^{-1}$;

$^1$H NMR (DMSO-d$_6$) δ: 7.4–7.3 (4H, m), 7.04 (2H, t, J=8.9 Hz), 6.9–6.7 (2H, m), 6.52 (1H, dd, J=1, 15:2 Hz), 5.16 (1H, dd, J=5.6, 15.7 Hz), 4.89 (1H, d, J=4.8 Hz), 4.72 (1H, d, J=5.5 Hz) 4.13 (1H, m), 4.04 (2H, q, J=7.2 Hz), 3.85 (1H, m), 3.75 (3H, s), 2.42, (1H, dd, J=4.6, 15 Hz), 2.28 (1H, dd, J=8.3, 15 Hz), 5.5 (1H, m), 4.2 (1H, m), 1.17 (3H, t, J=7.2 Hz);

$^{13}$C NMR (DMSO-d$_6$)δ: 171.02, 163.51, 163.05, 153.03, 145.34, 139.46, 136.34, 132.2 (d, $^3J_{C-F}$=8.3 Hz), 131.0 (d, $^{13}J_{C-F}$=9.1 Hz), 125.14, 121.64, 115.41 (d, $^2J_{C-F}$=20.4 Hz), 115.13, (d, $^2J_{C-F}$=21.1 Hz), 67.79, 64.76, 59.50, 44.10, 42.34, 33.44, 14.01 ppm;

Anal. Calcd. for C$_{25}$H$_{26}$F$_2$N$_4$O$_4$: C, 61.98; H, 5.41; N, 11.56 Found: C, 61.51; H, 5.67; N, 11.12.

EXAMPLE 9

Sodium (±)-erythro-9,9-bis(4-fluorophenyl)-3,5-dihydroxy-8-(1-methyl-1H-tetrazol-5-yl)-6,8-nonadienoate To a solution of ethyl 9,9-bis(4-fluorophenyl)-3,5-dihydroxy-8-(1-methyl-1H-tetrazol-5-yl)-6,8-nonadienoate (1.231 g, 2.54 mmoles) in 35 mL of tetrahydrofuran at 0° C. was added 1N NaOH solution 2.54 mL (1.0 equivalent) dropwise. The rate of addition should be slow enough to prevent the reaction mixture from changing color into deep amber or reddish. The reaction mixture was stirred for 30 minutes at 0° C. forming a clear homogeneous solution. The reaction mixture was allowed to warm to ambient temperature and saponification was allowed to proceed for an additional hour. Analytical TLC eluted with 20% MeOH in CHCl$_3$ (v/v) showed the desired product at R$_f$=0.2. Most of the organic solvent was evaporated at approximately 10° under reduced pressure (20 mmHg). The resulting thick syrup was diluted with 4 mL of water and then the solution was lyophilized at 0.01 mmHg to give 1.126 g (100%) of t he title compound as a sodium salt which appears to contain about one mole of water; m.p. >100° C. decomposed.

IR (KBr) $v_{max}$: 3400 (v.br), 1600 (s), 1575 (s), (1513 (s), 1438 (s), 1404 (s), 1225 (s), 1156 (s), 838 (s) cm$^{-1}$;

$^1$H NMR (DMSO-d$_6$) δ: 7.3–7.4 (4H, m), 7.06 (1H, br, D$_2$O exchangeable), 7.00–7.06 (2H, m), 6.87–6.91 (2H, m), 6.49 (1H, d, J=15.7 Hz), 5.13 (1H, dd, J=5.4, 15.7 Hz), 5.05 (1H, br D$_2$O exchangeable), 4.14 (1H, m), 3.74 (3H, s), 3.62 (1H, m), 1.99 (1H, dd, J=3.7, 13.5 Hz), 1.80 (1H, dd, J=8.5, 13.5 Hz), 1.43 (1H, m), 1.30 (1H, m);

$^{13}$C NMR (DMSO-d$_6$) δ: 175.87, 161.85 (d, $^1J_{C-F}$=246.1 Hz), 161.37 (d, $^1J_{C-F}$=246.9 Hz), 153.08, 144.97, 139.88, 136.40, 135.51, 132.22 (d, $^3J_{C-F}$=8.3 Hz), 130.97 (d, $^3J_{C-F}$=8.3 Hz) 124.66, 121.74, 115.42 (d, $^2J_{C-F}$=21.9 Hz), 115.12 (d, $^2J_{C-F}$=23.4 Hz), 68.23, 65.71, 44.50, 43.55, 33.45 ppm;

Anal. Calcd. for C$_{23}$H$_{21}$F$_2$N$_4$O$_4$Na H$_2$O: C, 55.64; H, 4.67; N, 11.28. Found: C, 55.24; H, 4.65; N, 10.85.

EXAMPLE 10

Trans-6-[4,4-bis(4-fluorophenyl)-3-(1-methyl-1H-tetrazol-5-yl)-1,3-butadienyl]-tetrahydro-4-hydroxy-2H-pyran-2-one.

A.

(±)-erythro-9,9-Bis(4-fluorophenyl)-3,5-dihydroxy-8-(1-methyl-1H-tetrazol-5-yl)-6,8-nonadienoic acid To a solution of ethyl (±)-erythro-9,9-bis(4-fluorophenyl)-3,5-dihydroxy-8-(1-methyl-1H-tetrazol-5-yl)-6,8-nonadienoate (0.64 g, 1.32 mmoles) in 25 mL of tetrahydrofuran at 0° C. was treated with 1.32 mL of 1.0 Molar NaOH solution. The pale yellow suspension was stirred at 0° C. for two hours forming a clear pale yellow solution. The crude reaction mixture was diluted with 5 mL of aqueous HCl (2N) solution and organic material was extracted into ethyl acetate (40 mL×2). The organic extracts were combined, dried over MgSO$_4$ and concentrated under reduced pressure to give a pale yellow gum. The crude dihydroxy acid was rigorously dried under high vacuum (0.01 mm Hg at room temperature for 24 hours) before submitting for the next step.

B.

Trans-6-[4,4-bis(4-fluorophenyl)-3-(1-methyl-1H-tetrazol-5-yl)-1,3 butadienyl]tetrahydro-4-hydroxy 2H-pyran-2-one The dry acid from the above Step A was dissolved in 100 mL of dry methylene chloride under argon at room temperature followed by the addition of 1.7 g (4.0 mmoles) of 1-cyclohexyl 3-(2-morpholinoethyl)carbodiimide metho-p-toluenesulphonate. Lactonization was complete in less than 15 minutes as indicated by analytical TLC (R$_f$= 0.12) eluted three times with 50% ethyl acetate in hexanes. Most of the solvent was evaporated under reduced pressure and the residue was washed with water (40 mL) followed by extractions with ethyl acetate (40 mL×2). The organic layers were combined, dried over MgSO$_4$ and concentrated under reduced pressure to give 0.54 g (89.7%) of the product. A pure sample of the product was obtained by passing through a short bed of silica gel eluted with 40% ethyl acetate in hexanes (v/v) to give the title compound which appears to contain about two moles of water. MS (CI): m/e=438 for (M+H)+;

IR (KBr) $v_{max}$: 3425 (br), 1738 (v.s.), 1600 (s), 1513 (s), 1225 (vs), 1156 (s), 1038 (s), 838 (s) cm$^{-1}$;

$^1$H NMR (CDCl$_3$) δ: 7.26–7.21 (2H, m), 7.14 (2H, d, J=8.7 Hz), 6.86 (4H, d, J=6.8 Hz), 6.72 (1H, dd, J=0.8, 15.6 Hz), 5.34 (1H, dd, J=7.1, 15.6 Hz), 5.18 (1H, m), 4.37 (1H, m), 3.57 (3H, s), 2.68 (1H, dd, J=4.5, 18 Hz), 2.60 (1H, ddd, J=3.63, 2.5, 18 Hz), 2.44 (1H, d, J=2.6 H$_2$, D$_2$O exchangeable), 2.00 (1H, dt, J=18, 1.7 Hz), 1.79 (1H, td, J=2.7, 18 Hz) ppm;

$^{13}$C NMR (CDCl$_3$) δ: 169.20, 163, 162.5, 153.20, 148.81, 135.61, 134.95, 132.45 (d, $^3J_{C-F}$=8 Hz), 132.52, 131.51, (d, $^3J_{C-F}$=8 Hz), 130.04, 120.44, 115.95, (d, $^2J_{C-F}$21.9 Hz), 115.83 (d, $^2J_{C-F}$=21.9 Hz), 75.67, 62.54, 38.58, 35.58, 33 64 ppm;

Anal. Calcd. for C$_{23}$H$_{20}$F$_2$N$_4$O$_3$ 2H$_2$O: C, 58.22; H, 5.10; N, 11.81 Found: C. 59.06; H, 4.45; N, 11.25.

A sample of the above lactone was crystallized from cyclohexane-benzene to give the title compound as a crystalline solid containing about one mole of benzene; m.p. =105°–106° C.

Anal. Calcd. for $C_{23}H_{20}F_2N_4O_3 \cdot C_6H_6$: C, 67.48; H, 5.07; N, 10.85
Found: C, 67 44; H, 5.Z3; N, 10.59.

EXAMPLE 11

4,4'-Difluoro-3,3'-dimethylbenzophenone

2-Fluorotoluene (8 ml, 73 mmoles) was added to a vigorously stirred mixture of aluminum chloride (61.43 g, 460 mmoles) and carbon tetrachloride (135 ml) at 0° C. After 10 minutes 2-fluorotoluene (92 ml, 837 mmoles) in carbon tetrachloride (75 mL) was added dropwise over 4 hours and the mixture stirred for 2 hours at 0° C. *WARNING: A spontaneous vigorous reaction occurred after the addition of 2-fluorotoluene.* The mixture was cooled to −20° C. and quenched with 2N HCl (250 mL). The organic layer was separated, washed with brine and dried ($MgSO_4$). The solvent was removed by evaporation and the residue dissolved in benzene (200 mL) and treated with water (200 mL) and acetic acid (50 ml). After stirring for 15 hours, the organic layer was separated, dried ($MgSO_4$) and evaporated. Crystallization from ethanol afforded 50 % (49%) of the title compound; m.p.=128°-130° C.

IR (KBr) $\nu_{max}$: 1650 cm$^{-1}$.

$^1$H NMR (CDCl$_3$) δ: 7.66 (d, J=7.3 Hz, 2H), 7.58 (m, 2H), 7.09 (t, J=8.8 Hz, 2H), 2.32 (s, 6H).

Anal. Calcd. for $C_{15}H_{12}F_2O$: C, 73.16; H, 4.91 Found: C, 72.96; H, 4.80.

EXAMPLE 12

1,1-Bis(4-fluoro-3-methylphenyl)-2-(1-methyl-1H-tetrazol-5-Yl) ethanol

A solution of 1,5-dimethyltetrazole (2.55 g, 26 mmoles) in dry tetrahydrofuran (15 ml) at −78° C. was treated with n-butyllithium (12.5 ml of a 2.5 M solution in hexane, 31.2 mmoles) and the mixture stirred for 15 minutes. 4,4'-Difluoro-3,3'-dimethylbenzophenone (5 g, 20.3 mmoles) in dry tetrahydrofuran (20 ml) was added, the mixture stirred for 1 hour, then quenched with 2N HCl (250 ml). The aqueous phase was extracted with ethyl acetate (3×50 ml) and the combined organic layer was dried (MgSO$_4$) and evaporated. The residue was purified by silica gel column chromatography using 20% (v/v) EtOAc-hexane as eluent to afford 3.7 g, (52%) of the product. Recrystallization from EtOAc-hexanes yielded the title compound; m.p. 41°-42° C.

IR (KBr) $\nu_{max}$: 3400 (br) cm$^{-1}$;

$^1$H NMR (CDCl$_3$) δ: 7.20 (d, J=7.1 Hz), 2M), 7.10 (m, 2H), 6.88 (t, J=8.6 Hz, 2H), 4.84 (s, 1H), 3.77 (s, 3H), 3.71 (s, 2H), 2.20 (s, 6H);

Anal. Calcd. for $C_{18}H_{18}F_2N_4O$: C, 62.79; H, 5.27; N, 16.27. Found: C, 62.73; H, 5.32; N, 16.16.

EXAMPLE 13

1,1-Bis(4-fluoro-3-methylphenyl)-2-(1-methyl-1H-tetrazol-5)ethene

A mixture of 1,1-bis(4-fluoro-3-methylphenyl)-2-(1-methyl-1H-tetrazol-5-yl)ethanol (3 58 g, 10.9 mmoles) and potassium hydrogen sulfate (530 mg) was heated at 195° C. for 1.5 hours. The mixture was cooled to 70° C. and chloroform (50 ml) was added. The insoluble material was removed by filtration and the filtrate evaporated. The residue was crystallized from EtOAc-Hexane to afford 3.38 g of the title compound; m.p.=138°-139° C.

$^1$H NMR (CDCl$_3$) δ: 7.20–6.80 (m, 6H), 6.65 (s, 1H), 3.56 (s, 3H), 2.28 (s, 3H), 2.18 (s, 3H).

Anal. Calcd. for $C_{18}H_{16}F_2N_4$: C, 66.25; H, 4.95; N, 17.17. Found: C, 66.15; H, 5.05; N, 17.24.

EXAMPLE 14

3,3-Bis(4-fluoro-3-methylphenyl)-2-(1-methyl-1H-tetrazol-5-yl)-2-propenal

A solution of 1,1-bis(4-fluoro-3.methylphenyl)-2-(1-methyltetrazol-5-yl)ethene (3.58 g, 11.0 mmoles)) in dry tetrahydrofuran (20 mL) at −78° C. was treated with n-butyllithium (5.3 ml of 2.5 M solution in hexane; 13.25 mmoles) and the mixture stirred at −78° C. for 0.5 hours. Ethyl formate (1.33 ml; 1.22 g, 16.5 mmoles) was added and the mixture was allowed to warm up to 23° C. over 1 hour, then quenched with 2N HCl (250 mL). The aqueous phase was extracted with ethyl acetate (3×50 mL) and the combined organic layers were dried (MgSO$_4$) and evaporated. The residue was purified by chromatography using 20% EtOAc-Hexane as eluent to afford 2.2 g (57%) of the title compound as a foam. MS (CI): m/e =355 for (M+H)$^+$;

IR (KBr) $\nu_{max}$: 1660 cm$^{-1}$;

$^1$H NMR (CDCl$_3$)δ: 9.62 (s, 1H), 7.25–7.05 (m, 3H), 6.85–6.65 (m, 3H), 3.73 (s, 3H), 2.34 (s, 3H), 2.13 (s, 3H).

Anal. Calcd. for $C_{19}H_{16}F_2N_4O$: C, 64.41; H, 4.56; N, 15.82.
Found: C, 64.60; H, 4.70, N, 15.62.

EXAMPLE 15

1,1-Bis(2,4-dimethylphenyl)-2-(1-methyl-1H-tetrazol-5-yl)ethanol.

A solution of 1,5-dimethyltetrazole (8.9 g, 91.0 mmoles) in 100 mL of dry tetrahydrofuran at −60° C. was treated with n-butyl lithium (48 mL of 1.89M solution, 91.0 mmoles). After stirring for 20 minutes, 2,2',4,4'tetramethylbenzophenone (18 g, 76 mmoles) [prepared by the procedure described in *J. Am. Chem. Soc.*, 81, 4858 (1959)] in 50 mL dry tetrahydrofuran was added and the solution was stirred for 1 hour during which time it was allowed to warm to −20° C. The reaction was quenched with 1N HCl, then extracted with chloroform. The combined organic extracts Were dried (MgSO$_4$) and evaporated to give 22 g of the title compound; m.p.=175°-177° C.

IR (KBr) $\nu_{max}$: 3390 (br), 1620 (s), 1460 (s), 1200 (s), 820 (s) cm$^{-1}$;

$^1$H NMR (CDCl$_3$)δ: 7.26 (2H, d), 6.95–6.83 (4H, m), 4.00 (1H, s), 3.82 (2H, s), 3.41 (3H, s), 2.23 (6H, s), 1.83 (6H, s) ppm;

$^{13}$C NMR (CDCl$_3$)δ: 152.34, 139.28, 137.32 135.79, 133.24, 126.26, 125.92, 77.47, 35.04, 32.99, 21.28, 20.76 ppm;

Anal. Calcd. for $C_{20}H_{24}N_4O$: C, 71.41; H, 7.20; N, 16.67 Found: C, 70.82; H, 7.26; N, 16.45.

EXAMPLE 16

1,1-Bis(2,4-dimethylphenyl)-2-(1-methyl-1H-tetrazol-5-yl)ethene.

A mixture of 1,1-bis(2,4-dimethylphenyl)-2-(1-methyl-1H-tetrazol-5-yl)ethanol (1.8 g, 5.4 mmoles) and potassium hydrogen sulfate (100 mg) in a 50 ml flask was placed in an oil bath preheated to 190° C. After 15 minutes, the melt was cooled and methylene chloride added to the residue. The insolubles were removed and the solution evaporated. The residue was crystallized from isopropyl ether to give 1.2 g of the title compound; m.p.=143°–143.5° C.

IR (KBr) $\nu_{max}$: 2930 (s), 1635 (s), 1620 (s), 1510 (s), 1450 (s), 820 (s), 740 (s) cm$^{-1}$;

$^1$H NMR (CDCl$_3$)$\delta$: 7.15–6.80 (6H, m), 6.60 (1H, s), 3.40 (3H, s), 2.36 (3H, s), 2.30 (3H, s), 2.18 (3H, s), 1.85 (3H, s) ppm;

$^{13}$C NMR (CDCl$_3$)$\delta$: 154.18, 152.21, 138.54, 138.38, 138.06, 135.67, 135.40, 135.18, 131.78, 131.72, 129.90, 129.66. 126.77, 126.55, 111.99, 33.65, 21.02, 20.69, 19.95 ppm;

Anal. Calcd. for C$_{20}$H$_{22}$N$_4$: C, 75.45; H, 6.97; N, 17.60 Found: C, 75.04; H. 7.03; N, 17.63.

EXAMPLE 17

3,3-Bis(2,4-dimethylphenyl)-2-(1-methyl-1H-tetrazol-5-yl)-2-propenal

A solution of 1,1-bis(2,4-dimethylphenyl)-2-(1-methyl-1H-tetrazol-5-yl)ethene (1.0 g, 3.1 mmoles) in 10 mL dry tetrahydrofuran was treated with n-butyl lithium (1.64 mL of 1.89 M solution, 3.1 mmoles) at −78° C. After stirring with cooling for 30 minutes, ethyl formate (0.3 g, 4.0 mmoles) was added and the mixture stirred with cooling for 2 hours. The reaction was quenched with 1N HCl and extracted with chloroform. The combined organic fractions were dried (MgSO$_4$) and evaporated. The residue was purified by column chromatography on silica gel eluting with 10% (v/v) ethyl acetate in hexane to give 0.9 g of product as an oil. Trituration of the oil with isopropyl ether gave the title compound as a solid; m.p.=117°–120° C. MS (CI): m/e=347 for (M+H)$^+$;

$^1$H NMR (CDCl$_3$)$\delta$: 9.58 (1H, s), 7.25–6.78 (7H, m), 3.70 (3H, s), 2.40 (3H, s), 2.25 (3H, s), 2.20 (3H, s), 1.90 (3H, s) ppm;

$^{13}$C NMR (CDCl$_3$)$\delta$: 189.49, 168.80, 151.05, 140.87, 140.26, 137.06, 135.86, 134.87, 133.28, 132.04, 129.60, 126.62, 125.28. 34.17, 21.21, 21.06, 20.37, 20.07 ppm;

Anal. Calcd. for C$_{21}$H$_{22}$N$_4$O: C, 72.81; H, 6.41; N, 16.18; Found: C, 72.99; H, 6.43; N, 16.09.

EXAMPLE 18

3,3-Bis(4-fluorophenyl)-2-(1-methyl-1H-tetrazol-5-yl)propenal

A. 1,1-Bis(4-fluorophenyl)-2-(1-methyl-1H-tetrazol-5-yl)ethanol

To a solution of 1,5-dimethyltetrazole (0.98 g, 10.0 mmoles) in tetrahydrofuran (20 mL) at −30° C. was added n-butyl lithium (4.7 mL of 2.14M solution, 10.0 mmoles). After stirring for 0.25 hour, the solution was cooled to −50° C. and 4,4′-difluorobenzophenone (1.74 g, 8.0 mmoles) was added. After stirring for 1 hour at −50° C. and 1 hour at −10° C., the reaction was quenched with 1N hydrochloric acid. The mixture was extracted with methylene chloride, dried and evaporated in vacuo. The residue was purified by column chromatography on silica gel eluting with 40% (v/v) ethyl acetate in hexane to give 2.0 g of the title compound; m.p.=116°–118° C.

Anal. Calcd for C$_{16}$H$_{14}$F$_2$N$_4$O: C, 60.76; H, 4.47; N, 17.72 Found: C, 60.62; H, 4.52; N, 17.63

B. 1,1-Bis(4-fluorophenyl)-2-(1-methyl-1H-tetrazol-5-yl)ethene

A mixture of 1,1-bis(4-fluorophenyl)-2-(1-methyl-1H-tetrazol-5-yl)ethanol (4.2 g, 12.7 mmoles) [prepared in Step A] and potassium hydrogen sulfate was heated at 195° C. for 0.5 hour. After cooling, the mixture was dissolved in chloroform and washed with water. The organic layer was dried and evaporated in vacuo. The residue was triturated with diethyl ether to give 3.9 g of the title compound; m.p.=169°–171° C.

Anal. Calcd. for C$_{16}$H$_{12}$F$_2$N$_4$: C, 64.43; H, 4.06; N, 18.88 Found C, 63.93; H, 4.00; N, 19.25.

3,3-Bis(4-fluorophenyl)-2-(1-methyl-1H-tetrazol-5-yl)propenal

To a finely divided suspension of 1,1-bis(4-fluorophenyl)-2-(1-methyl-1H-tetrazol-5-yl)ethene (1.0 g, 3.3 mmoles) [prepared in Step B] in tetrahydrofuran (10 mL) at −80° C. was added n-butyl lithium (1.54 mL of 2.14 M solution), 3.3 mmoles) with the formation of a dark violet color. After stirring for 40 minutes at −80° C., ethyl formate (0.32 g, 4.3 mmoles) was added and the mixture stirred for 2.5 hours at −80° C. The mixture was hydrolyzed with 1N hydrochloric acid and extracted with methylene chloride. The extracts were dried (MgSO$_4$) and evaporated in vacuo. The residue was triturated with diethyl ether to give 0.77 g of yellow solid, m.p. 128°–131° C. The solid was crystallized from isopropyl acetate-hexane to give 0.55 g of the title compound; m.p.=130°–132° C.

Anal. Calcd. for C$_{17}$H$_{12}$F$_2$N$_4$O: C, 62.58; H, 3.71; N, 17.18. Found: C, 62.15; H, 3.82; N, 16.75.

EXAMPLE 19

3,3-Bis(4-fluorophenyl)-2-(1-methyl-1H-tetrazol-5-yl-2-propenal

A. 5-Ethyl-1-methyl-1H-tetrazole

To a slurry of 1,5-dimethyltetrazole (4.9 g, 0.05 mole) in dry tetrahydrofuran (50 mL) was added 2.5M n-butyllithium in hexanes (20 mL, 0.05 mole) over a period of 15 minutes at −78° C. under an inert atmosphere. This mixture was stirred for 30 minutes and a yellowish precipitate formed during this time. Methyl iodide (3.7 mL, 0.06 mole) was then added over a period of 15 minutes. After stirring for an additional 30 minutes, the clear reaction mixture was diluted with water and extracted with ethyl acetate (3×50 mL). The aqueous layer was washed with chloroform (2×25 mL), and the combined organic layer was dried over sodium sulfate and concentrated under reduced pressure to give an oil. The oil was purified by distillation to give 5.2 g (92%) of the title compound; b.p. =89°–90° C. at 0.05 mm Hg.

$^1$H NMR (CDCl$_3$)$\delta$: 4.05 (s, 3H), 2.86 (q, 2H), 1.41 (t, 3H);

$^{13}$C NMR (CDCl$_3$)$\delta$: 156.0, 33.24, 16.75, 11.20.

B. 1,1-Bis(4-fluorophenyl)-2-(1-methyl-1H-tetrazol-5-yl)propanol

To a solution of 5-ethyl-1-methyl-1H-tetrazole (5.6 g, 0.05 mole) [prepared in Step A] in 60 mL of dry tetrahydrofuran was added 2.5M n-butyllithium (20 mL, 0.05 mole) in hexane over 5 minutes at −78° C. (bath temperature) under an inert atmosphere. The mixture was stirred for 30 minutes and a solution of 4,4′-difluorobenzophenone (10.8 g, 0.5 mole) in 25 mL of dry tetrahydrofuran was added over 5 minutes. This mixture was stirred for an additional 2 hours while the bath temperature was slowly warmed to −20° C. The reaction was quenched with 1N HCl and extracted with ethyl acetate (3×50 mL) and chloroform (3×50 mL). The combined organic layer was dried over sodium sulfate and concentrated under reduced pressure to give a white solid. The solid was purified by crystallization from ethanol-hexane to give 10.8 g (65%) of the title compound; m.p.=160°–161° C.

IR (KBr) $\nu_{max}$: 3400 cm$^{-1}$;

$^1$H NMR (CDCl$_3$)$\delta$: 7.8–7.02 (m, 8H), 5.95 (s, 1H), 4.65 (q, 1H), 3.98 (s, 3H), 1.29 (d, 2H).

$^{13}$C NMR (CDCl$_3$)$\delta$: 162.57, 162.37, 159.14, 156.71, 142.48, 140.54, 128.25, 128.13, 127.52, 127.42, 114.67, 114.41, 114.38, 78.56, 36.99, 33.43, 14.52.

Anal. Calcd. for C$_{17}$H$_{16}$F$_2$N$_4$O: C, 61.81; H, 4.88; N, 16.96 Found: C, 61.79; H, 4.90; N, 17.09.

C.
1,1-Bis(4-fluorophenyl)-2-(1-methyl-1H-tetrazol-5-yl)-1-propene

A slurry of 1,1-bis(4-fluorophenyl)-2-(1-methyl-1H-tetrazol-5-yl)propanol (8.25 g, 0.025 mole) [prepared in Step B] and 100 mg of p-toluene sulfonic acid monohydrate in xylene (60 mL) was heated to reflux with a Dean & Stark water collecting apparatus for a period of 12 hours. The reaction mixture was washed with 1N NaOH (10 mL) while it was warm and with water (100 mL). Concentration of the organic layer gave off-white crystals of product. This was purified by recrystallization from ethanol-hexane to give 7.1 g (91%) of the title compound as white crystals; m.p.=146°–147° C.

IR (KBr)$\nu_{max}$: 1575; 1500 cm$^{-1}$.

$^1$H NMR (CDCl$_3$)$\delta$: 7.42–6.85 (m, 8H), 3.53 (s, 3H), 2.14 (s, 3H);

$^{13}$C NMR (CDCl$_3$)$\delta$: 163.37, 163.08, 160.13, 155.61, 144.60, 145.34, 136.47, 136.42, 136.24, 136.19, 131.65, 131.54, 131.11, 131.01, 119.53, 115.51, 115.27, 115.22, 33.50, 21.20.

Anal. Calcd. for C$_{17}$H$_{14}$F$_2$N$_4$:
C, 65.37; H, 4.51; N, 17.94
Found: C, 65.64; H, 4.61; N, 18.09.

D.
3,3-Bis(4-fluorophenyl)-1-bromo-2-(1-methyl-1H-tetrazol-5-yl)-2-propene A slurry of 1,1-bis(4-fluorophenyl)-2-(1-methyl-1H-tetrazol-5-yl)-1-propene (61.46 g, 0.197 mole) [prepared in Step C], N-bromosuccinimide (35.06 g, 0.197 mole) and catalytic amount of azobis isobutyronitrile or benzoyl peroxide in carbon tetrachloride (1.2 liters) was heated to reflux in an inert atmosphere for a period of 2 hours. The reaction mixture was cooled to ambient temperature and the solid from the reaction was filtered. The filtrate was concentrated under reduced pressure and the solid obtained was recrystallized from toluene-hexane to give 72 g (93%) of the title compound as white crystals; m.p.=159°–160° C.

IR (KBr)$\nu_{max}$: 1600 cm$^{-1}$.

$^1$H NMR (CDCl$_3$)$\delta$: 7.5–7.1 (m, 8H), 4.44 (s, 2H), 3.53 (s, 3H).

$^{13}$C NMR (CDCl$_3$)$\delta$: 163.94, 163.74, 160.60, 160.45, 143.42, 149.68, 135.20, 135.15, 134.69, 131.43, 131.31, 130.90, 130.80, 119.57, 115.94, 115.77, 115.65, 115.50.

Anal. Calcd. for C$_{17}$H$_{13}$F$_2$BrN$_4$: C, 52.19; H, 3.34; N, 14.32 Found: C, 52.58; H, 3.47; N, 14.49.

E.
3,3-Bis(4-fluorophenyl)-2-(1-methyl-1H-tetrazol-5-yl)-2-propenal

To a solution of sodium ethoxide (3.93 g of sodium metal, 0.17 mole) in 500 mL of absolute ethanol was added 2-nitropropane (16.66 g, 0.187 mole) slowly over 5 minutes. The bromo compound prepared in the above Step D (67.1 g, 0.17 mole) was added portionwise over a period of 10 minutes. The reaction mixture was stirred for 2 hours and the ethanol was removed in vacuo. The residue was dissolved in CH$_2$Cl$_2$ (500 mL), washed with water (250 mL) and dried over sodium sulfate. The organic layer was concentrated under reduced pressure to give an oil. The oil was dissolved in hot toluene (350 mL) and trituration with hexane (350 mL) gave 50.6 E (91%) of the title compound as white crystals; m.p.=135°–137° C.

EXAMPLE 20
[1,1-Bis(4-fluorophenyl)-2-(1-methyl-1H-tetrazol-5-yl)-1-propen-3-yl]triphenylphosphonium bromide A slurry of 3,3-bis(4-fluorophenyl)-1-bromo-2-(1-methyl-1H-tetrazol-5-yl)-2-propene (1.95 g, 0.005 mole) [prepared in Example 19, Step D] and triphenylphosphine (1.3 g, 0.005 mole) in cyclohexane (25 mL) was heated to reflux. The reaction mixture became a clear solution after 30 minutes and a white precipitate appeared after 1 hour. The mixture was heated for an additional 8 hours, cooled to ambient temperature and the solid was collected by filtration and washed with diethyl ether. This white powder was dried in vacuum at 50° C. to give 3.0 g (92%) of the title compound; m.p.=254°–255° C.

IR (KBr)$\nu_{max}$: 3450, 1600, 1500, 1425 cm$^{-1}$.

$^1$H NMR (DMSO-d$_6$)$\delta$: 7.92–6.80 (m, 23H), 4.94 (6d, 2H), 3.83 (s, 3H);

$^{13}$C NMR (DMSO-d$_6$)$\delta$: 163.53, 163.36, 160.28, 160.87, 154.04, 153.89, 152.76, 135.11, 134.79, 134.16, 133.68, 133.54, 130.53, 130.45, 130.35, 130.21, 130.07, 118.02, 116.89, 116.18, 115.89, 115.62, 115.32, 111.43, 111.39. 34.22, 28.88, 28.22.

Anal. Calcd for C$_{35}$H$_{28}$BrF$_2$N$_4$P: C, 64.31; H, 4.32; N, 8.57 Found: C, 64.02; H, 4.37; N, 8.89.

EXAMPLE 21
Methyl (±)-erythro-9,9-bis(4-fluorophenyl)-3,5-dihydroxy-8-(1-methyl-1H-tetrazol-5-yl)-6,8-nonadienoate To a slurry of the phosphonium bromide (0.326 g, 0.5 mmole) [prepared in Example 20] and methyl erythro-3,5-bis(diphenyl-t-butylsilyloxy)-6-oxo-hexanoate [prepared according to the general procedures described by P. Kapa, et al. in Tetrahedron Letters, 2435–2438 (1984) and in U.S. Pat. No. 4,571,428, issued Feb. 18, 1986 to P. K. Kapa] (0.26 g, 0.4 mmole) in dry dimethylformamide (1 mL) was added potassium t-butoxide (0.067 g, 0.6 mmole) at −20° C. (bath temperature) in an inert atmosphere. The slurry became a red solution and was stirred for 18 hours at −10° C. The reaction was worked up by adding ammonium chloride solution (10 mL) and extracting with methylene chloride (2×30 mL). The organic layer was dried over sodium sulfate and concentrated to give an oil. The oil was purified through a pad of silica gel and the major fraction was isolated as an oil (160 mg). The oil (160 mg) was stirred with 1M tetra-n-butyl ammonium fluoride solution in tetrahydrofuran (2 mL) and few drops of glacial acetic acid for a period of 18 hours. The reaction mixture was poured into water (10 mL) and extracted with ethyl acetate (3×20 mL). The organic layer was dried over sodium sulfate and concentrated to given an oil. The oil was purified by silica gel flash column chromatography eluting with ethyl acetate;hexane (2:1) to give 0.08 g (75%) of the title compound as an oil. MS (CI): m/e=471 for (M+H)+;

$^1$H NMR (CDCl$_3$)δ: 7.26–6.6 (m, 9H), 5.37 (dd, 1H), 4.44 (m, 1H), 4.24 (m, 1H), 3.71 (s, 3H), 3.56 (s, 3H), 2.47 (d, 2H), 1.58 (m, 2H).

A more polar fraction was also isolated (20 mg) and identified as the corresponding trans lactone.

EXAMPLE 22

4,4'-Difluoro-2,2'-dimethylbenzophenone

To a well stirred mixture of aluminum chloride (6.1 g, 46.0 mmoles) in carbon tetrachloride (14 mL) at 0° C., 3-fluorotoluene (1 g from a total of 10 g, 90.0 mmoles) was added and the mixture stirred for 10 minutes. The remainder of the 3-fluorotoluene in 9 mL of carbontetrachloride was added and the mixture stirred at 0° C. for 4 hours. The mixture was cooled to −20° C. and hydrolyzed by adding 25 mL 1N hydrochloric acid. The organic layer was separated and concentrated in vacuo. The residue was stirred for 16 hours with a mixture of benzene (20 mL), water (20 mL), and acetic acid (5 mL). The aqueous layer was separated and extracted with diethyl ether. The combined organic fractions were dried (MgSO$_4$) and concentrated in vacuo. Analytical TLC of the residue showed 3 spots; R$_f$=0.67, 0.59 and 0.56[5% (v/v) ethyl acetate in hexane on silica gel]. Column chromatography on silica gel with 0.5% (v/v) ethyl acetate in hexane and collection of the appropriate fractions containing material having R$_f$=0.67[5% (v/v) ethyl acetate in hexane] gave 1.3 g of the title compound; m.p.=50°–52° C. MS (CI): m/e=247 for (M+H)+;

$^1$H NMR (CDCl$_3$)δ: 7.26 (2H, dd), 6.96 (2H, dd), 6.87 (2H, dt), 2.42 (6H, s).

Anal. Calcd. for C$_{15}$H$_{12}$F$_2$O: C, 73.17; H, 4.92 Found: C, 73.34; H, 5.02.

EXAMPLE 23

1,1-Bis(4-fluoro-2-methylphenyl)-2-(1-methyl-1H-tetrazol-5-yl)ethanol

To a suspension of 1,5-dimethyltetrazole (3.8 g, 39.0 mmoles) in tetrahydrofuran (40 mL) at −40° C. was added butyl lithium (17.7 mL of a 2.2 M solution, 39.0 mmoles). After stirring for 10 minutes, 4,4'-difluoro-2,2'-dimethylbenzophenone (8 g, 32.5 mmoles) was added and the solution stirred for 3 hours. The reaction was quenched with 1N hydrochloric acid. The aqueous layer was separated and extracted With ethyl acetate. The combined organic phases were dried (MgSO$_4$) and concentrated in vacuo to give 7.5 g of the title compound; m.p.=186°–188° C.

Anal. Calcd. for C$_{18}$H$_{18}$F$_2$N$_4$O: C: 62.99; H, 5.27; N, 16.27 Found: C: 63.01; H, 5.34; N, 16.18.

EXAMPLE 24

1,1-Bis(4-fluoro-2-methylphenyl)-2-(1-methyl-1H-tetrazol-5-yl)ethene

A mixture of 1,1-bis-(4-fluoro-2-methylphenyl)-2-(1-methyl-1H-tetrazol-5-yl)ethanol (0.5 g, 1.5 mmoles) and p-toluenesulfonic acid (0.2 g) was heated at reflux in toluene (30 mL) for 16 hours. The mixture was cooled, diluted with diethyl ether (50 mL) and extracted with saturated sodium bicarbonate solution and water. The organic layer was dried (MgSO$_4$) and concentrated in vacuo.

The residue was triturated with diethyl ether to give 0.3 g of the title compound; m.p.=120°–125° C.

Anal. Calcd. for C$_{18}$H$_{16}$F$_2$N$_4$: C, 66.25; H, 4.95; N, 17.17 Found: C. 66.55; H, 4.92; N. 16.84.

EXAMPLE 25

3,3-Bis(4-fluoro-2-methylphenyl)-2-(1-methyl-1H-tetrazol-5-yl)-2-propenal

To a solution of 1,1-bis(4-fluoro-2-methylphenyl)-2-(1-methyl-1H-tetrazol-5-yl)ethene (1.6 g, 5.0 mmoles) in tetrahydrofuran at −70° C. was added butyl lithium (2.3 mL of 2.2 M solution, 5.0 mmoles). After stirring for 0.25 hour, ethyl formate (0.44 g, 6.0 mmoles) was added and the mixture stirred for 2 hours. The reaction was quenched with 1N hydrochloric acid and the mixture was extracted with methylene chloride. The extracts were dried and concentrated in vacuo to give 1.0 g of the title compound; m.p.=135°–136° C.

Anal. Calcd. for C$_{19}$H$_{16}$F$_2$N$_4$O: C, 64.41; H, 4.56; N, 15.82 Found: C, 64.22; H, 4.59; N, 15.50.

EXAMPLE 26

5,5-Bis(4-fluoro-2-methylphenyl)-4-(1-methyl-1H-tetrazol-5-yl)-2,4-pentadienal

A solution of 3,3-bis(4-fluoro-2-methylphenyl)-2-(1-methyl-1H-tetrazol-5-yl)-2-propenal (0.88 g, 2.5 mmoles) and triphenylphosphoranylidene acetaldehyde (0.75 g, 2.5 mmoles) in benzene (50 mL) was heated at reflux for 3 hours. The solvent was removed by evaporation and the crude residue purified by column chromatography on silica gel eluting with 1% (v/v) methanol in methylene chloride. The fractions containing material having R$_f$=0.9 [1:20 (v/v) methanolmethylene chloride] were combined and concentrated to give 0.8 g of the title compound; m.p.=75°–95° C. MS: M+=380;

$^1$H NMR (CDCl$_3$)δ: 9.52 (1H, d), 7.30–6.67 (7H, m), 5.82 (1H, dd), 3.62 (3H, s), 2.23 (3H, s), 2.00 (3H, s).

Anal. Calcd. for C$_{21}$H$_{18}$F$_2$N$_4$O: C, 66.31; H, 4.78; N, 14.73 Found: C, 65.76; H, 4.85; N, 14.52.

EXAMPLE 27 tert-Butyl 9,9-bis(4-fluoro-2-methylphenyl)-5-hydroxy-8-(1-methyl-1H-tetrazol-5-yl)-3-oxo-6,8-nonadienoate To a solution of 5,5-bis(4-fluoro-2-methylphenyl)-4-(1-methyl-1H-tetrazol-5-yl)-2,4-pentadienal (1.0 g, 2.5 mmoles) in tetrahydrofuran at −50° C. was added the dianion of t-butyl acetoacetate (2.5 mL of a 1M solution, 2.5 mmoles) prepared by adding t-butyl acetoacetate (4.0 g, 25.0 mmoles) in tetrahydrofuran (4 mL) to a suspension of sodium hydride (1.0 g of 60% dispersion, 25.0 mmoles) in tetrahydrofuran at −5° C. followed by cooling to −30° C. and the addition of butyl lithium (11.4 mL of 2.2M solution, 25 mmoles). After stirring for 1.5 hours, analytical TLC indicated starting aldehyde and another 0.5 mL of dianion solution was added. The solution was stirred an additional 0.5 hour and quenched with 1N hydrochloric acid. The mixture was extracted with methylene chloride. The extracts were dried and concentrated in vacuo. The residue was purified by column chromatography on silica gel eluting with methanol in methylene chloride to produce 0.6 g of the title compound; m.p.=65°-72° C.

Anal. Calcd. for $C_{29}H_{32}F_2N_4O_4$: C, 64,68;H, 5.99; N, 10.41. Found: C, 64.50; H, 5.98; N, 10.16.

EXAMPLE 28 tert-Butyl (±)-erythro-9,9-bis(4-fluoro-2-methylphenyl)-3,5-dihydroxy-8-(1-methyl-1H-tetrazol-5-yl)6,8-nonadienoate To a solution of t-butyl 9,9-bis(4-fluoro-2-methylphenyl)-5-hydroxy-8-(1-methyl-1H-tetrazol-5-yl)-3-oxo-6,8-nonadienoate (2.5 g, 4.6 mmoles) in tetra hydrofuran (30 mL) at −5° C. was added triethylborane (6.0 mL of a 1M solution, 6.0 mmoles) and the solution stirred for 1 hour. After cooling to −78° C., sodium borohydride (0.36 g, 9.0 mmolos) and methanol (2 mL) were added. The mixture was stirred at −78° C. for 2 hours and diluted with hexane (15 mL). The mixture was hydrolyzed with 1N hydrochloric acid. The aqueous layer was separated and extracted with methylene chloride. The combined organic solutions were dried and concentrated in vacuo. The residue was dissolved in methanol and the solution stirred for 18 hours. The solution was concentrated in vacuo and the residue purified by column chromatography on silica gel eluting with 1% (v/v) methanol in methylene chloride to produce 1.7 g of the title compound as a white powder; m.p.=75°-80° C.

$^1$H NMR (CDCl$_3$) δ: 7.15–6.60 (7H, m), 6.43 (1H, d), 5.26 (1H, dd), 4.42 (1H, m), 4.18 (1H, m), 3.92 (1H, s). 3.64 (3H, s), 2.39 (2H, d), 2.26 (3H, bs), 2.04 (3H. s). 1.57 (2H, m), 1.43 (9H. s);

Anal. Calcd. for $C_{29}H_{34}F_2N_4O_4$: C, 64.44; H, 6.34; N, 10.37 Found (corr. for 0.28% H$_2$O): C, 64.14; H, 6.41; N, 10.16.

EXAMPLE 29

Sodium (±)-erythro-9,9-bis(4-fluoro-2-methylphenyl)-3.5-dihydroxy-8-(1-methyl-1H-tetrazol-5-yl)-6,8-nonadienoate To a solution of t-butyl 9,9-bis(4-fluoro-2-methylphenyl)-3,5-dihydroxy-8-(1-methyl-1H-tetrazol-5-yl)-6,8-nonadienoate (1.65 g, 3.05 mmoles) in ethanol (50 mL) was added sodium hydroxide (3.05 mL of 1N solution, 3.05 mmoles) and the solution stirred at room temperature for 3 hours and at 50° C. for 1 hour. The solution was concentrated in vacuo to give 1.3 g of the title compound which appears to contain about one mole of water; m.p.=225°−225° C. (dec.).

Anal. Calcd. for $C_{25}H_{35}F_2N_4O_4$Na H$_2$O: C, 57.26; H, 5.19; N, 10.69 Found: C, 57.30; H, 5.20; N, 10.00.

EXAMPLE 30

2,2'-Difluoro-4,4'-dimethylbenzophenone

Concentration of the appropriate fractions from the silica gel column chromatography of Example 22 having material with $R_f$=0.56 and trituration of the residue with hexane gave 1.2 g of the title compound; m.p.=84°-85.5° C.

$^1$H NMR (CDCl$_3$) δ: 7.57 (2H, t, $J_{H-H}$=8 Hz, $J_{FH}$=8 Hz), 7.02 (2H, d, $J_{H-H}$=8 Hz), 6.89 (2H, d, $J_{FH}$=8 Hz), 2.39 (6H, s).

Anal. Calcd. for $C_{15}H_{12}F_2O$): C, 73.17; H, 4.92 Found: C, 73.19; H, 4.88.

EXAMPLE 31

1,1-Bis(2-fluoro-4-methylphenyl)-2-(1-methyl-1H-tetrazol-5-yl)ethanol

To a solution of 1,5-dimethyltetrazole (4.6 g, 4.7 mmoles) in tetrahydrofuran (40 mL) at −50° C. was added butyl lithium solution (21.4 mL of a 2.2 M solution, 4.7 mmoles). After stirring for 10 minutes, a solution of 2,2'-difluoro-4,4'-dimethylbenzophenone in tetrahydrofuran (15 mL) was added. The solution was stirred for 2.5 hours during which time it was allowed to warm to −10° C. The reaction was quenched by adding 1N hydrochloric acid. The layers were separated and the aqueous layer was extracted with methylene chloride. The combined organic fractions were dried (MgSO$_4$) and evaporated. The residue was triturated with diethyl ether and crystallized from isopropyl acetate to give 8.0 g of the title compound; m.p=150°-151° C. MS: M$^+$ = 344.

Anal. Calcd. for $C_{18}H_{18}F_2N_4O$: C, 62.79; H, 5.27; N, 16.27 Found: C, 26.84; H, 5.23; N, 16.28.

EXAMPLE 32

1,1-Bis(2-fluoro-4-methylphenyl)-2-(1-methyl-1H-tetrazol-5-yl)ethene

A suspension of 1,1-bis(2-fluoro-4-methylphenyl)-2-(1-methyl-1H-tetrazol-5-yl)ethanol (7.3 g, 21.0 mmoles) in toluene (200 mL) with p-toluene sulfonic acid (3 g) and the mixture heated at reflux for 14 hours. After cooling, the mixture was diluted with diethyl ether and extracted with saturated sodium bicarbonate solution and water. The organic layer was dried (MgSO$_4$) and evaporated. The residue was triturated with isopropyl ether to give the title compound; m.p.=58°-60° C.

Anal. Calcd for $C_{18}H_{16}F_2N_4$: C, 66.25; H, 4.95; N, 17.17 Found: C, 66.27; H, 4.94; N, 16.93.

EXAMPLE 33

3,3-Bis(2-fluoro-4-methylphenyl)-2-(1-methyl-1H-tetrazol-5-yl)-2-propenal

To a solution of 1,1-bis(2-fluoro-4-methylphenyl)-2-(1-methyl-1H-tetrazol-5-yl)ethene (1.6 g, 5.0 mmoles) in tetrahydrofuran (20 mL) at −78° C. was added butyl lithium (2.3 mL of a 2.2 M solution, 5 mmoles). After stirring for 15 minutes, ethyl formate (0.44 g, 6.0 mmoles) was added and the solution stirred with cooling for 2 hours. The reaction was quenched with 1N hydrochloric acid and the mixture extracted with diethyl ether. The extracts were dried (MgSO$_4$) and evaporated. The residue was crystallized from isopropyl acetate to give 0.66 g of the title compound; m.p.=154°-155° C.

Anal Calcd. for $C_{19}H_{16}F_2N_4O$: C, 64.41; H, 4.56; N, 15.82 Found: C, 64.44; H, 4.63; N, 15.58.

EXAMPLE 34

Ethyl 1-Methyl-5-tetrazolylacetate

To a solution of 1,5-dimethyltetrazole (10 g) in 100 mL of dry tetrahydrofuran and 20 mL of hexamethylphosphoramide at −78° C. (dry ice-acetone) under an argon atmosphere was added dropwise 50 mL (1.2 equivalent) of n-butyllithium (2.5M in hexane). The deprotonation of 1,5-dimethyltetrazole was allowed to proceed at −78° C. for 40 minutes, then at −20° C. for 30 minutes. The anion solution was rechilled to −78° C. and transferred via a cannula over a period of 45 minutes into a cold (−78° C.) solution containing 12 mL of ethyl chloroformate in 50 mL of tetrahydrofuran. The reaction mixture was diluted with aqueous 2N HCl and saturated aqueous solution of sodium chloride and then extracted with ethyl acetate. The residue from the organic extract was purified by silica gel flash chromatography. The appropriate fractions were combined and evaporated to give 4 g of product. The product was further purified by crystallization from ethyl acetate-hexanes to yield 3.52 g (21%) of the title compound; m.p.=64°–66° C.

Anal. Calcd. for $C_6H_{10}N_4O_2$: C, 42.35; H, 5.92; N, 32.92 Found: C, 42.40; H, 5.98; N, 33.15.

EXAMPLE 35

Ethyl 3.3-bis(4-fluorophenyl)-2-(1-methyl-1H-tetrazol-5-yl)-2-propenoate

A mixture of titanium tetrachloride (2 mL) and carbon tetrachloride (2 mL) was added to 15 mL of tetrahydrofuran at −78° C. under an argon atmosphere. The suspension was stirred at −78° C. for 30 minutes before 0.2 g of 4,4′-difluorobenzophenone was added. After stirring for an additional 30 minutes, a solution of 0.15 g of ethyl 1-methyl-5-tetrazolylacetate in 1 mL of dry pyridine was added dropwise. The dark brownish suspension was stirred at −78° C. for 15 minutes, then was allowed to warm to 0° C. forming a thick paste. The mixture was allowed to stand for 24 hours at ambient temperature before it was poured into water. The aqueous mixture was extracted with ethyl acetate to yield crude product. Analytical TLC eluted five times with 20g (v/v) ethyl acetate in hexanes showed the desired product at $R_f$=0.3. Pruification by preparative chromatography on two 20×20 $cm^2$ 0.25 mm TLC plates eluted twice with 20% (v/v) ethyl acetate in hexanes to give the title compound which was identical to the compound of Example 3.

EXAMPLE 36

Dimethyl [3,3-bis(4-fluorophenyl)-2-(1-methyl-1H-tetrazol-5-yl)-2-propen-1-yl]phosphonate A slurry of 3,3-bis-(4-fluorophenyl)-1-bromo-2-(1-methyl-1H-tetrazol-5-yl)-2-propene (1.17 g, 3.0 mmol) and trimethyl phosphite (0.41 g, 3.3 mmol) was heated at 100° C. for 5 minutes. After cooling to ambient temperature, excess trimethylphosphite was removed in vacuo to give a light yellow solid. This solid was recrystallized from ethylacetate/hexane mixture to give the title compound as a pure white solid; m.p.=140°–141° C.

IR (KBr)$\nu_{max}$: 1604, 1511 $cm^{-1}$;

$^1$H NMR (CDCl$_3$) δ: 7.7–6.8 (8H, m), 3.6 (3H, s), 3.5 (3H,s), 3.42 (3H, s), 3.2 (2H, d);

Anal. Calcd. for $C_{19}H_{19}F_2O_3N_4P$: C, 54.29; H, 4.56; N, 13.33 Found: C, 53.83; H, 4.48; N, 13.50.

EXAMPLE 37

Methyl (±)-erythro-9,9-bis(4-fluorophenyl)-3,5-dihydroxy-8-(1-methyl-1H-tetrazol-5-yl)-6,8-nonadienoate To a solution of the phosphonate (0.84 g, 2.0 mmol) [prepared in Example 36] was added one equivalent of n-BuLi (2.0 mmol) at −78° C. (dry ice/acetone) and the resulting deep red-colored solution was stirred at −78° C. for 15 minutes Methyl erythro -3,5-bis (diphenyl-t-butylsilyloxy)-6-oxohexanoate [prepared according to the general procedures described by P. Kapa, et al., in Tetrahedron Letters 2435–2438 (1984) and in U.S. Pat. No. 4,571,428, issued Feb. 18, 1986 to P. Kapa] (1.30 g, 2.0 mmol) in THF (2 mL) was added and the mixture stirred for 24 hours. The reaction mixture was allowed to warm to room temperature during the course of this time. The reaction was quenched by adding 5 mL) of NH$_4$Cl and then extracted with ethyl acetate (2×20 mL). The organic layer was dried (Na$_2$SO$_4$) and evaporated under reduced pressure to a yellow oil. The oil was stirred with 1M-tetra-n-butyl ammonium fluoride solution in tetrahydrofuran (4 mL) containing a few drops of glacial acetic acid for a period of 24 hours. The reaction mixture was poured into water (20 mL) and extracted with methylene chloride (3×20 mL). The organic layer was dried (Na$_2$SO$_4$), concentrated, and the oil was purified by silica gel flash column chromatography eluting with ethyl acetate: hexane (2:1) to give 0.284 g (41%) of the title compound as an oil. MS (CI): m/e=471 for (M+H) ;

$^1$H NMR (CDCl$_3$)δ: 7.26–6.6 (9H, m), 5.29 (1H, dd), 4.42 (1H, m), 4.28 (1H, m), 3.69 (3H, s), 3.54 (3H, s), 2.42 (2H, d), 1.5 (2H, m).

EXAMPLE 38

1-(4-Fluorophenyl)-2-(1-methyl-1H-tetrazol-5-yl)-1-phenylethanol

A solution of 1,5-dimethyltetrazole (29.25 g; 0.298 mole) in dry THF (400 mL) was cooled to −78° C. and treated with n-butyllithium (133 mL of a 2.5M solution in hexane; 0.3325 mole) over 30 minutes. The mixture was stirred at −78° C. for 30 minutes and treated with 4-fluorobenzophenone (50 g; 0.25 mole). The mixture was stirred at −78° C. for 30 minutes and allowed to warm up to 23° C. over 2 hours. The reaction was quenched with 2N HCl (100 mL) and the organic solvent was removed by evaporation. The residue was extracted with CHCl$_3$ (2×100 mL) and the combined organic layers were dried (Na$_2$SO$_4$) and evaporated to afford a brown oil. Purification by chromatography using 20% EtOAc-hexane as eluent afforded the title compound as a white solid (46.3 g; 62%). m.p.=113°–114° C. (crystallized from EtOAc-hexane). MS (CI): m/e=299 for (M+H)$^+$;

IR (KBr) $\nu_{max}$: 3300 (br), 1605, 1510 $cm^{-1}$;

$^1$H NMR δ: 7.34–7.15 (m, 7H), 6.93 (m, 2H), 4.93 (s, 1H), 3.73 (s, 2H), 3.67 (s, 3H) ppm;

$^{13}$C NMR δ: 163.57, 160.29, 152.28, 144.94, 141.12, 141.08, 128.43, 127.87, 127.75, 127.67, 125.76, 115.25, 114 96, 77.03, 35.82, 33.45 ppm;

Anal. Calcd. for $C_{16}H_{15}FN_4O$: C, 64.42; H, 5.07; N, 18.79 Found: C, 64.32; H, 5.05; N, 18.84

EXAMPLE 39

(E)-1-(4-Fluorophenyl)-2-(1-methyl-1H-tetrazol-5-yl)-1-phenylethene and(Z)-1-(4-Fluorophenyl)-2-(1.methyl-1H-tetrazol-5-yl)-1-phenylethene A mixture of the tetrazolyl ethanol (3.2 g; 10.74 mmole) (prepared in Example 38) and potassium hydrogen sulfate (800 mg) was heated at 195° C. for 30 minutes. After cooling to 100° C., chloroform (30 mL) was added and the mixture triturated until most of the solid had dissolved. The insoluble inorganic material was removed by filtration and the solvent removed by evaporation to afford a mixture of the title compounds as a light brown solid (2.8 g; 93%). Crystallized from EtOAc-hexane. MS (CI): m/e=281 for (M+H)+;

IR (KBr) $\nu_{max}$: 1640, 1600, 1510, 1445, 1220 cm$^{-1}$;

$^1$H NMR δ: 7.50–6.90 (m, 9H), 6.75 (s, 1H), 3.60 (s,1.7H), 3.43 (s, 1.3H) ppm;

$^{13}$C NMR δ: 165 19, 164.58, 161.26, 153.14, 152.97, 152.22, 152.13, 140.53, 137.81, 136.71, 133.99, 133.94, 131.74, 131.62, 130.38, 129.67, 129.29, 128.85, 128.65, 128.38, 115.97, 115.74, 115.66, 115.45, 108.29, 108.15, 33.70 ppm;

Anal Calcd. for $C_{16}H_{13}FN_4$: C, 68.56; H, 4.68; N, 19.99 Found: C, 68.63; H, 4.77; N, 20.37

EXAMPLE 40

(E)-3-(4-Fluorophenyl)-2-(1-methyl-1H-tetrazol-5-yl)-3-phenylpropenal and (Z)-3-(4-fluorophenyl)-2-(1-methyl-1H-tetrazol-5-yl)-3-phenylpropenal A suspension of the olefin (20 g; 71.43 mmole) (prepared in Example 39) in dry THF (200 mL) was cooled to −78° C. and treated with n-butyllithium (31.5 mL of 2.5M solution in hexane; 78.75 mmole) and the resulting mixture stirred at −78° C. for 30 minutes. Ethyl formate (6.9 g; 93 mmole) was added and the mixture stirred at −78° C. for 2 hours and allowed to warm up to 23° C. over 1 hour. The reaction was quenched with 2N HCl (100 mL). the organic solvent was removed by evaporation and the residue extracted with EtOAc (3×75 mL). The combined organic layers were dried (MgSO$_4$), evaporated and the residue purified by chromatography using 35% EtOAc-hexane as eluent to afford the title compound as a mixture of aldehydes (7.75 g; 35%). MS (CI): m/e=309 for (M+H)+;

$^1$H NMR δ: 9.67 (s, 0.66H), 9.64 (s,0.33H), 7.70–6.90 (m, 9H), 3.74 (s, 1H), 3.68 (s, 2H) ppm;

EXAMPLE 41

(E),(E)-5-(4-Fluorophenyl)-4-(1-methyl-1H-tetrazol-5-yl)-5-phenyl-2,4-pentadienal A mixture of the mixed aldehydes (5.1 g; 16.56 mmole) (prepared in Example 40) and formylmethylenetriphenylphosphorane (5.05 g; 16.56 mmole) and benzene (200 mL) was heated together under reflux in a nitrogen atmosphere for 2 hours.

The solvent was removed by evaporation and the residue purified by chromatography using 30% EtOAc-hexane as eluent to afford the product as an orange foam (4.56 g). Fractional crystallization from EtOAc-hexane afforded the title compound as orange crystals (0.93 g; 17%); m.p.=137°–138° C. (crystallized from EtOAc-hexane). MS (CI): m/e=335 for (M+H)+;

$^1$H NMR δ: 9.54 (d, J=7.5 Hz, 1H), 7.47 (d, J=15.6 Hz, 1H), 7.35–6.80 (m, 9H), 5.84 (dd, J=7.4 Hz, J′=15.7 Hz, 1H), 3.50 (s, 3H) ppm;

$^{13}$C NMR δ: 192.54, 147.86, 132.09, 131.97, 130.64, 130.41, 128.96, 116.17, 115.87, 33.62 ppm.

EXAMPLE 42

Ethyl (E),(E)-9-(4-fluorophenyl)-5-hydroxy-8-(1-methyl-1H-tetrazol-5-yl)-9 phenyl-3-oxonona-6,8-dienoate A suspension of sodium hydride (175 mg; 80% dispersion; 5.83 mmole) in dry THF (10 mL) was cooled to 0° C. and treated with ethyl acetoacetate (725 μL; 740 mg; 5.69 mmole) and stirred at 0° C. for 10 minutes. Butyllithium (2.3 mL of 2.5M solution; 5.75 mmole) was added and the mixture stirred at 0° C. for 15 minutes. A solution of the aldehyde (860 mg; 2.57 mmole) (prepared in Example 41) in dry THF (10 mL) was added and the mixture stirred at 0° C. for 15 minutes. The reaction was quenched by the addition of 2N HCl (30 mL) and the organic solvent removed by evaporation. The residue was extracted with EtOAc and the combined organic extracts were dried (MgSO$_4$) and evaporated. The residue was purified by chromatography using 40% EtOAc-hexane as eluent to afford the title compound as a yellow gum (954 mg; 80%). MS (CI): m/e=465 for (M+H)+;

IR (film)$\nu_{max}$: 3400 (br), 1730, 1600, 1510 cm$^{-1}$;

$^1$H NMR δ: 7.20–6.60 (m, 9H), 6.54 (d, J=15.6 Hz, 1H). 5.16 (dd, 1H), 4.40 (br, 1H), 4.00 (q and br, 3H), 3.31 (s, 3H), 3.25 (s, 2H), 2.52 (m, 2H), 1.08 (t, 3H) ppm.

EXAMPLE 43

Ethyl (±)-(E),(E)-erythro-9-(4 fluorophenyl)-3,5-dihydroxy-8-(1-methyl-1H-tetrazol-5-yl) 9-phenylnona-6,8-dienoate A solution of the β-ketoester (950 mg; 2.045 mmole) (prepared in Example 42) in dry THF(20 mL) was treated with a solution of triethylborane (2.25 mL of 1M soln. in THF; 2.25 mmole) and stirred at 23° C. for 1 hour. Methanol (400 μL) was added and the mixture cooled to −78° C. and treated with NaBH$_4$ (200 mg; 5.26 mmole). After 1 hour the reaction was quenched by the addition of 2N HCl and the organic solvent removed by evaporation. The residue was extracted with EtOAc and the combined organic extracts were dried (MgSO$_4$) and evaporated. The residue was purified by chromatography using 60% EtOAc-hexane as eluent to afford the title compound as a yellow gum (330 mg; 35%). MS (CI): m/e=467 for (M+H)+;

IR (KBr)$\nu_{max}$: 3400 (br), 1725, 1600, 1500 cm$^{-1}$;

$^1$H NMR δ:7.30–6.80 (m, 9H), 6.70 (dd, J=1.0 Hz J′=15.6 Hz, 1H), 5.35 (dd, J=5.9 Hz, J′=15.7 Hz, 1H), 4.41 (m, 1H), 4.25 (br s, 1H), 4.15 (q, J=7.1 Hz, 2H), 3.83 (br m, 2H), 3.52 (s, 3H), 2.45 (d, J=6.1 Hz, 2H), 1.60 (m, 2H), 1.26 (t, J=6.1 Hz, 3H) ppm;

$^{13}$C NMR δ: 172.40, 164.47, 161.17, 153.66, 148.07, 139.94, 138.21, 137.75, 135.55, 132.40, 132.30, 130.36, 129.82, 129.46, 128.67, 128.47, 127.29, 121.05, 115.74, 115.45, 71.89, 69.35, 68.34, 60.83, 60.34, 42.34, 41.53, 41.22, 33.56, 14.13 ppm.

EXAMPLE 44

Sodium (±)-(E),(E)-erythro-9-(4-fluorophenyl)-3,5-dihydroxy-8-(1-methyl-1H-tetrazol-5-yl)-9-phenylnona-6,8-dienoate hydrate A solution of the dihydroxyester (160 mg; 0.343 mmole) (prepared in Example 43) in EtOH (5 mL) was treated with 1N NaOH (343 μL; 0 343 mmole) and the resulting solution stirred at 23° C. for 1 hour. The solvent was removed by evaporation and the residue was dissolved in water (2 mL) and lyophilized to afford the title compound as a light brown solid (155 mg); m.p.=130°–137° C.

IR (KBr)$\nu_{max}$: 3400 (br), 1560, 1510 cm$^{-1}$;

$^1$H NMR (DMSO-d$_6$) δ: 7.50–6.80 (m, 9H), 6.51 (d, J=15.7 Hz, 1H), 5.15 (dd, J=5.4 Hz, J′=15.7 Hz. 1H), 4.15 (m, 1H), 3.70 (s, 3H), 3.65 (br, 1H), 3.35 br, 2H). 1.95 (m, 2H), 1.40 (m, 2H) ppm;

$^{13}$C NMR (DMSO-d$_6$)δ: 176.42, 163.42, 153.17, 146.07, 140.03, 139.73, 135.70, 135.64, 132.20, 132.09, 128.72, 128.42, 128.07, 127.98, 124,83, 121.51, 115.51, 115.22, 66.22, 65.69, 44.46, 43.59, 33.42 ppm.

Anal. Calcd. for $C_{23}H_{22}FN_4O_4Na \cdot H_2O$: C, 57.74; H, 5.06; N, 11.72 Found: C, 58.70; H, 5.10; N, 11.16.

EXAMPLE 45

2(1-Methyltetrazol-5-yl)-1,1-diphenylethanol

A solution of 1,5-dimethyltetrazole (20 g; 0.204 mole) in dry THF (200 mL) was cooled to −78° C. and treated with n-butyllithium (91 mL of 2.5 molar solution in hexane; 0.227 mole) and the mixture stirred at −78° C. for 30 minutes. Benzophenone (31.1 g; 0.171 mole) was added and the mixture stirred at −78° C. for 30 minutes and allowed to warm up to 23° C. and stirred for 15 hours. The mixture was quenched with 2N HCl (100 mL) and extracted with EtOAc (3×150 mL). The combined organic layers were dried (MgSO$_4$) and evaporated. The residue was crystallized from EtOAc-Hexane to afford the title compound as a white solid (10.5 g; 22%); m.p.=175°–176° C. (crystallized from EtOAc-hexane). MS (CI): m/e=281 for (M+H)$^+$;

IR (KBr)$\nu_{max}$: 3300 (br), 1530, 1500 cm$^{-1}$;

$^1$H NMR δ: 7.50–7.20 (m, 10H), 5.45 (s, 1H), 3.82 (s, 2H), 3.80 (s, 3H) ppm;

$^{13}$C NMR δ: 152.36, 145.63, 128.16, 127.28, 126.05, 125.94, 77.70, 35.90, 33.76 ppm;

Anal. Calcd. for $C_{16}H_{16}N_4O$: C, 68.56; H, 5.76; N, 20.00 Found: C, 68.62; H, 5.81; N, 20.10.

EXAMPLE 46

2,2-Diphenyl-1-(1-methyltetrazol-5-yl)ethene

A mixture of 2(1-methyltetrazol-5-yl)-1,1-diphenylethanol (2.15 g; 7.68 mmole) and KHSO$_4$ (300 mg) was heated at 200° C. for 20 minutes. The cooled mixture (50° C.) was triturated with CHCl$_3$ (50 mL) and the organic solvent was decanted from the inorganic residue. Evaporation afforded the title compound as a cream solid (1.7g; 85%); m.p.=147°–148° C. (crystallized from EtOAc-hexane). MS (CI): m/e=263 for (M+H)$^+$;

IR (KBr)$\nu_{max}$: 1640, 1500, 1445 cm$^{-1}$;

$^1$H NMR δ: 7.50–7.00 (m, 10H), 6.78 (s, 1H), 3.43 (s, 3H) ppm;

$^{13}$C NMR δ: 153.94, 152.18, 140.40, 137.83, 129.54, 129.37, 128.94, 128.59, 128.38, 128.28, 108.22, 33.56 ppm.

Anal. Calcd. for $C_{16}H_{14}N_4$: C, 73.27; H, 5.38; N, 21.36 Found: C, 73.25; H, 5.43; N, 21.43.

EXAMPLE 47

3,3-Diphenyl-2-(1 methyl-1H-tetrazol-5-yl)propenal

A solution of 2,2-diphenyl-1-(1-methyl-1H-tetrazol-5-yl)ethene (3.75 g; 14.29 mmole) in dry THF (40 mL) was cooled to −78° C. and treated with n-butyllithium (6.3 mL of a 2.5M soln. in hexane; 15.75 mmole) and the resulting mixture stirred at −78° C. for 30 minutes. Ethyl formate ( 1.5 mL; 18.58 mmole) was added and the mixture stirred at −78° C. for 2 hours. The reaction was quenched with 2N HCl and the solvent removed by evaporation. The residue was extracted with EtOAc (3×30 mL) and the combined organic layers were dried (MgSO$_4$) and orated. The residue was purified by chromatography using 25–35% EtOAc-hexane as eluent to afford starting material (1.35 g; 36%) and the desired title compound (1.65 g; 39%); m.p.=185°–186° C. (crystallized EtOAc-hexane). MS (EI): m/e=290 for M$^+$;

IR (KBr)$\nu_{max}$: 1675, 1600, 1445 cm$^{-1}$;

$^1$H NMR δ: 9.66 (s, 1H), 7.70–6.90 (m, 10H), 3.66 (s, 3H) ppm;

$^{13}$C NMR δ: 189.45, 167.79, 151.44, 138.35, 136.65, 131.54, 131.34, 130.96, 129.63, 128.71, 123.55, 33.91 ppm.

Anal. Calcd. for $C_{17}H_{14}N_4O$: C, 70.34; H, 4.87; N, 19.30 Found: C, 70.63; H, 4.99; N, 19.33.

EXAMPLE 48

(E)-4-(1-Methyl-1H-tetrazol-5-yl)-5.5-bis(phenyl)-2.4-pentadienal

A solution of the aldehyde 11.33 g; 4.57 mmole) (prepared in Example 47) and triphenylphosphoranylidene acetaldehyde (1.5 g; 4.87 mmole) was heated under reflux in benzene (50 mL) for 24 hours. The solvent was evaporated and the residue was purified by chromatography using 30% EtOAc-hexane as eluent to afford the title compound as a yellow foam (1 g; 71%). MS (CI): m/e=317 (M+H)$^+$;

$^1$H NMR δ: 9.53 (d, J=7.5 Hz, 1H), 7.55–7.10 (m, 10H), 6.69 (d, J=16 Hz, 1H), 5.84 (dd, J=16 Hz, J'=7.5 Hz, 1H), 3.50 (s, 3H) ppm.

EXAMPLE 49

Methyl (E)-9,9-diphenyl-3,5-dihydroxy-8-(1-methyl-1H-tetrazol-5-yl)-nona-6 8-dienoate Methylacetoacetate(0.525 mL; 4.87 mmole) was added to a suspension of sodium hydride(0.160 g; 80% disp. in mineral oil) in THF at 0° C. and stirred for 10 minutes. N-Butyllithium (2.14 mL; 2.5M solution in hexanes) was added and reaction stirred for 15 minutes. This solution was added to a solution of the aldehyde(1.0 g; 3.2 mmole) (prepared in Example 48) in THF at 0° C. and stirred for 30 minutes. The reaction was treated with 2N HCl (30 mL) and extracted with EtOAc (3×15 mL). The organic layer was dried with MgSO$_4$ and evaporated. The crude residue was triturated with hexane (3×25 mL) then dissolved in THF/CH$_3$OH (4:1; 20 mL) and treated with triethylborane 13.2 mL; 1M solution in THF). Air was bubbled through the solution for 10 minutes and the reaction stirred for an additional 50 minutes. The solution was then cooled to −78° C. and treated with sodium borohydride (120 mg; 3.2 mmole) and sitrred for 1 hour. The reaction was quenched with 2M HCl (100 mL) and extracted with EtOAc (3×20 mL). The organic layers were dried with MgSO$_4$ and evaporated. The residue was dissolved in CH$_3$OH (30 mL) and stirred for 15 hours. The solvent was evaporated and residue purified by chromatography using 50% EtOAc-hexane as eluent to afford the title compound as a yellow oil (470 mg; 33%). MS (CI): m/e=435 (M+H)$^+$;

$^1$H NMR 7.80–6.80 (m, 10H), 6.71 (d, J=16 Hz, 1H), 5.34 (dd, J=16 Hz, J'=6 Hz, 1H), 4.60–4.10 (m, 2H), 3.70 (s, 3H), 3.52 (s, 3H), 2.45 (d, J=6 Hz, 2H), 1.70–1.50 (m, 2H) ppm.

EXAMPLE 50

Sodium (±) (E)-erythro-9 9-diphenyl-3,5-dihydroxy-8-(1-methyl-1H-tetrazol-5-yl)-nona-6,8-dienoate hydrate The methyl ester (470 mg; 1.08 mmole) (Prepared in Example 49) was dissolved in ethanol (10 mL) and treated with 1N NaOH (1.08 mL). The reaction was stirred for 1 hour. The solvent was evaporated and residue was freeze-dried to afford a light yellow powder (500mg; 100%); m.p.=145°-150° C.

IR $\nu_{max}$: 3400 (br), 1610, 1425, 1360 cm$^{-1}$;

$^1$H NMR (DMSO-d$_6$)δ: 7.60–6.60 (m,10H). 6.52 (d, J=16 Hz. 1H), 5.12 (dd, J=16 Hz, J'=5.5 Hz, 1H). 4.20–4.05,(m,1H), 3.80–3.55 (m, 1H),3.70 (s, 3H), 3.10 (br s, 2H) 2.10–1.10 (m, 5H) ppm.

Anal. Calcd. for C$_{23}$H$_{23}$N$_4$O$_4$Na.H$_2$O: C, 59.99; H, 5.47; N, 12.17 Found: C, 59.18; H, 5.46; N, 10.96.

EXAMPLE 51

2,2-Bis(4-methoxyphenyl)-1-(1-methyl-1H-tetrazol-5-yl)ethene

A solution of 1,5-dimethyltetrazole (20 g; 0.204 mole) in dry THF (200 mL) was cooled to −78° C. and treated with n-butyllithium (91 mL of 2.5M solution in hexane; 0.227 mole) 1 and the mixture stirred at −78° C. for 30 minutes. 4,4-Dimethoxybenzophenone (41.3 g; 0.171 mole) was added and the mixture stirred at −78° C. for 30 minutes, and allowed to warm up to 23° C. over 2 hours. The mixture was acidified with 2N HCl (100 mL) and the organic solvent removed by evaporation. The residue was extracted with EtOAc (3×300 mL) and the combined organic layers were dried (MgSO$_4$) and evaporated The residue was crystallized from EtOAc-hexane to afford a light brown solid (48 g) which was found to be a mixture of the desired Product and the initial aldol adduct (1,1-bis(4-methoxyphenyl)-2-(1-methyl-1H-tetrazol-5-yl)ethanol). This mixture was dissolved in xylene (180 mL) and heated under reflux for 1 hour with P-toluenesulfonic acid in a Dean-Stark apparatus. The cooled mixture was diluted with ether (100 mL) and the resulting solid removed by filtration to afford the title compound as a cream solid (40g); m.p.=146°-147° C. (crystallized from EtOAc-hexane). MS (CI): m/e=3Z3 for (M+H$^+$);

IR (KBr) $\nu_{max}$: 1605, 1520, 1250 cm$^{-1}$;

$^1$H NMR δ: 7.31 (d, J =7.8 Hz, 1H), 6.98 (d, J=7.8 Hz, 1H). 6.90 (d, J=7.8 Hz, 1H), 6.81 {d, J=8.6 Hz. 1H), 6.62 (s, 1H), 3.8(s, 3H), 3.79 (s, 3H), 3.42 {s, 3H) ppm;

$^{13}$C NMR δ: 160.79, 160.16. 153.29, 133.33, 131.25 130.32, 129.95, 127.36, 114.14, 113.69, 105.57, 55.40, 55.28, 33.71 ppm.

Anal. Calcd. for : C$_{18}$H$_{18}$N$_4$O$_2$: 67.07; H, 5.63; N, 17.38 Found: C, 66.93; H, 5.63; N, 17.05.

EXAMPLE 52

3.3-Bis(4-methoxyphenyl)-2-(1-methyl-1H-tetrazol-5-yl)Propenal

A solution of the olefin {4.6g; 14.29 mmole) (prepared in Example 51) in dry THF (50 mL) was cooled to −78° C. and treated with n-butyllithium (6.3 mL of a 2.5M solution in hexane; 15.75 mmole) and the resulting solution stirred at −78° C. for 30 minutes. Ethyl formate (1.5 mL) was added and the mixture stirred at −78° C. for 2 hours. The mixture was quenched with 2N HCl and the organic solvent removed by evaporation. The residue was extracted with EtOAc (3x30 mL) and the combined organic layers were dried (MgSO$_4$) and evaporated . The residue was purified by column chromatography using 25–35% EtOAc-hexane as eluent to afford starting material (0.84 g; 18%). Further elution afforded the desired title compound (1.78g; 36%); m.p.=130°-131° C. (crystallized from EtOAc-hexane). MS (CI) m/e 351 for (M+H)$^+$;

IR (KBr) $\nu_{max}$: 1675, 1605, 1515, 1260 cm$^{-1}$;

$^1$H NMR δ: 9.59 (s, 1H), 7.30 (d, J=8.6 Hz, 1H)' 7.00 (d. J=8.7 Hz. 1H). 6.90 (d, J=8.9 Hz. 1H), 6.74 (d. J=8.7 Hz. 1H). 3.90 (s, 3H). 3.77 (s, 3H). 3.67 (s, 3H) ppm;

$^{13}$C NMR δ: 189.51, 167.47, 162.59, 161.98, 152.30, 133.91. 132.29, 130.79, 129.35, 121.05, 114.20, 114.15, 55.80, 55.40. 33.94 ppm.

Anal. Calcd. for C$_{19}$H$_{19}$N$_4$O$_3$C, 65.14; H, 5.18; N, 15.99 Found: C, 64.96; H, 5.22; N, 15.75.

EXAMPLE 53

5.5-Bis-(4-methoxyphenyl)-2-(1-methyl-1H-tetrazol-5-yl)penta-2,4-dienal

A solution of 3,3-bis14-methoxyphenyl)-2-(1-methyl-1H-tetrazol-5.yl)Propenal (1.7 g; 4.86 mmole) in benzene (100 mL) was treated with triphenylphosphoranylidene acetaldehyde (1.55 g; 5.I mmole) and heated under reflux for 3 hours. The solvent was removed by evaporation and the residue Purified by chromatography using 30% EtOAc-hexane as eluent to afford the title compound as a yellow foam (1.35g; 74%). MS (CI): m/e=377 for (M+H)$^+$;

IR (KBr) $\nu_{max}$: 1675, 1590, 1510 cm$^{-1}$;

$^1$H NMR δ: 9 52 (d, J=7.6 Hz, 1H), 7.53 (d, J=14.2 Hz, 1H), 7.23 (d, J=8.5 Hz, 1H), 7.00 (d, J=9.3 Hz, 1H), 6.86 (d, J=9.Z Hz, 1H), 6.70 (d, J=8.9 Hz, 1H), 5.83 (dd, J=7.6 Hz, J'=15.7 Hz, 1H), 3.91 (s, 3H), 3 75 (s, 3H), 3 50 (s, 3H) ppm;

$^{13}$C NMR δ: 192.89, 161.40, 160.97, 157 91, 153.29, 149.41, 133.90, 132.77, 132.29, 132,00, 131.71, 131.65, 131.25, 130.81, 117.21, 114.18, 114.18, 55.49, 55.32, 33.61 ppm.

EXAMPLE 54

Ethyl (E)-9,9-bis(4-methoxyphenyl)-5-hydroxy-8-(1-methyl.1H-tetrazol-5-yl)-3-oxonona-6,8-dienoate Ethyl acetoacetate (825 μL; 842 mg; 6.48 mmole) was added to a suspension of NaH (206 mg; 80% dispersion; 6.68 mmole) in dry THF (20 mL) at 0° C. and the resulting mixture stirred at 0° C. for 10 minutes. A solution of n-butyllithium (2.7 mL of 2.5 M solution in hexane; 6.75 mmole) was added and the mixture stirred at 0° C. for 10 minutes. A solution of the aldehyde (1.3 g; 3.46 mmole) (prepared in Example 53) in dry THF (20 mL) was added and the mixture stirred at 0° C. for 15 minutes. After 2N HCl was added to quench the reaction, the solvent was removed by evaporation. The residue was diluted with water (30 mL), extracted with EtOAc (2×2 mL) and the combined organic layers were dried (MgSO$_4$) and evaporated. The residue was purified by chromatography using 40% EtOAc-hexane as eluent to afford the title compound as a yellow foam (1.165g; 66%).

IR (KBr) $\nu_{max}$: 3450 (br). 1750, 1710, 1610, 1510 cm$^{-1}$;

$^1$H NMR δ: 7.30 6.60 {m, 9H], 5.27 (dd, J=6.1 Hz, J'=15.9 Hz, 1H), 4.68 (brs, 1H), 4.14 (q, J=7.1 Hz, 2H)' 3.83 (s.3H), 3.69 (s.3H). 3.47 (s, 3H), 3.43 (s, 2H), 3.17 (brs. 1H), 2.70 (d, J=6.0 Hz, 2H), 1.23 (t, J=6.0 Hz, 3H) ppm;

$^{13}$C NMR δ: 202.48. 160.09, 159.70, 154.16, 149.40, 134.16, 132.57, 132.14, 131.99, 131.22, 129.08, 118.34, 113.79, 68.17, 61.47, 55.34, 55.17, 49.94, 49.33, 33.56, 14.09 ppm.

EXAMPLE 55

Ethyl (±)-(E)-erythro-9,9-bis(4-methoxyphenyl)-3,5-dihydroxy-8-(1-methyl-1H-tetrazol 5-yl)nona-6,8-dienoate A solution of the β-ketoester (1 g; 1.97 mmole) (prepared in Example 54) in dry THF (50 mL) and methanol (300 mL) was treated with a solution of triethylborane (2.15 mL of 1M in THF) and the mixture stirred at 23° C. for 1 hour. The solution was cooled to −78° C. and treated with NaBH$_4$ (110 mg; 2.9Z mmole). After 1 hour at -78° C the reaction was quenched with 2N HCl and the solvent was removed by evaporation. The residue was diluted with water and extracted with EtOAc (3×30 mL). The combined organic extracts were dried (MgSO$_4$) and evaporated. The residue was purified by chromatography to afford the title compound as a light oil (136mg).

IR (KBr) $\nu_{max}$: 3450 (br), 1750, 1710, 1610, 1510 cm$^{-1}$.

$^1$H NMR δ: 7.70–6.50 (m. 9H). 5.80 (dd, 1H), 4.45 (br, 1H), 4.15 (q, 2H), 3.85 (s, 3H), 3.72 (s, 3H), 3.50 (s, 3H), 2.45 (m, 2H), 1.55 (m, 2H). 1.26 (t, 3H) ppm 13C NMR δ: 172.38, 160.18, 159.29, 154.32, 148.92, 138.54, 136.19. 132.81, 132.29, 132.20, 132.11, 131.90. 131.51, 131.22, 128.59, 128.41, 128.36, 118.97, 113.90, 113.34. 72.15, 66.31, 60.75, 55.35, 55.20, 42.74, 42.14, 41.73, 41.48, 33.50, 14.18.

EXAMPLE 56

Sodium (±)-(E)-erythro-9.9-bis(4-methoxyphenyl)-3,5-dihydroxy-8-(1-methyl-1H-tetrazol-5-yl)nona-6,8-dienoate dihydrate A solution of the ester (95 mg; 0.196 mmole) (prepared in Example 55) in ethanol (15 mL) was treated with 1N NaOH solution (196 μL) and the mixture stirred at 23° C. for 1 hour. The solvent was removed by evaporation and the residue was dissolved in water (2 mL) and freeze dried to afford the title compound as a brown powder (95mg; 100%); m.p.=175°–180° C.

IR (KBr) $\nu_{max}$: 3400 (br), 1600, 1575, 1510 cm$^{-1}$;

$^1$H NMR (DMSO-d$_6$)δ: 7.70–6.65 (m, 9H), 6.55 (d, J=15.5 Hz, 1H), 5.08 (dd, J=5.6 Hz, J'=15.7 Hz, 1H), 4.14 (br, 1H), 3.75 (s, 3H), 3.67 (s, 3H), 3.66 (s, 3H), 2.10–1.80 (br, 2H), 1.50–1.20 (br, 2H) ppm;

13C NMR (DMS-d$_6$) δ: 159.25, 158.80, 153.78, 138.13, 132.75, 131.88, 131.60, 131.42, 131.30, 130.41, 128.68, 128.53, 125.72, 113.74, 113.48, 68.56, 65.89, 55.14, 54.99, 44.68, 43.68, 33.34.

Anal. Calcd. for C$_{25}$H$_{27}$NaN$_4$O$_6$.2H$_2$O: C, 55.76; H, 5.81; N, 10.41 Found: C, 54.43; H, 5.04; N, 8.15.

What is claimed is:

1. A compound of the formula

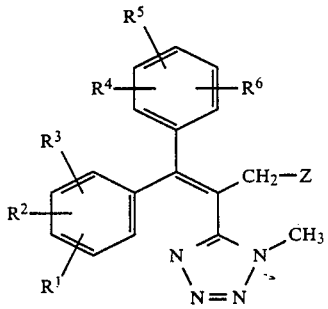

wherein
R$^1$ and R$^4$ each are independently hydrogen, halogen, C$_{1-4}$ alkyl, C$_{1-4}$ alkoxy or trifluoromethyl;
R$^2$, R$^3$, R$^5$ and R$^6$ each are independently hydrogen, halogen, C$_{1-4}$ alkyl or C$_{1-4}$ alkoxy;
Z is

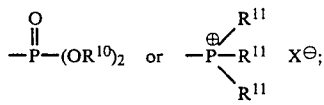

R$^0$ is C$_{1-4}$ alkyl; and
R$^{11}$ is phenyl which is unsubstituted or substituted by one or two C$_{1-4}$ alkyl or chloro substituents.

2. A compound of claim 1 wherein Z is triphenylphosphonium bromide.

3. A compound of claim 2 wherein R$^1$, R$^2$, R$^3$, R$^4$, R$^5$ and R$^6$ each are selected from the group consisting of hydrogen, fluoro, methyl and methoxy.

4. A compound of claim 1 wherein Z is dimethyl phosphonate.

5. A compound of claim 4 wherein R$^1$, R$^2$, R$^3$, R$^4$, R$^5$ and R$^6$ each are selected from the group consisting of hydrogen, fluoro, methyl and methoxy.

6. The compound of claim 1 which is [1,1-bis-(4-fluorophenyl)-2-(1-methyl-1H-tetrazol-5-yl)-1-propen-3-yl]triphenylphosphonium bromide.

7. The compound of claim 1 which is dimethyl [3,3-bis(4-fluorophenyl)-2-(1-methyl-1H-tetrazol-5-yl)-2-propen-1-yl]phosphonate.

8. A process for preparing a compound of the formula

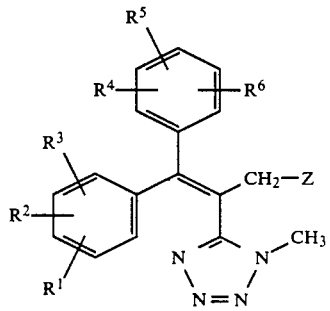

wherein R$^1$ and R$^4$ each are independently hydrogen, halogen, C$_{1-4}$ alkyl, C$_{1-4}$ alkoxy or trifluoromethyl; R$^2$, R$^3$, R$^5$ and R$^6$ each are independently hydrogen, halogen, C$_{1-4}$ alkyl or C$_{1-4}$ alkoxy and Z is

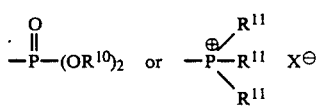

in which $R^{10}$ is $C_{1-4}$ alkyl; $R^{11}$ is phenyl which is unsubstituted or substituted by one or two $C_{1-4}$ alkyl or chloro substituents and X is bromo, chloro or iodo, comprising the steps of (a) reacting a benzophenone compound of the formula

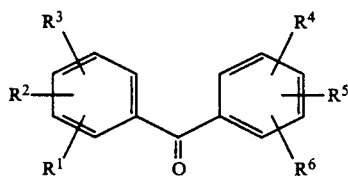

wherein $R^1$, $R^2$, $R^3$, $R^4$, $R^5$ and $R^6$ are as defined above with 5-ethyl-1-methyl-1H-tetrazole, to produce a compound of the formula

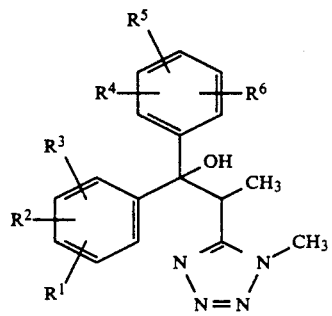
VIIa wherein $R^1$, $R^2$, $R^3$, $R^4$, $R^5$ and $R^6$ are as defined above;

(b) dehydrating an alcohol of Formula VIIa to produce a compound of the formula

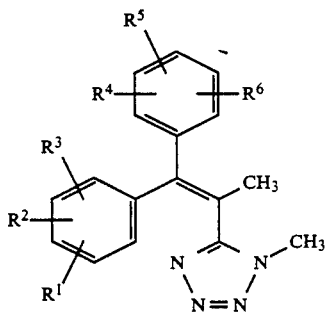
Id wherein $R^1$, $R^2$, $R^3$, $R^4$, $R^5$ and $R^6$ are as defined above;

(c) halogenating an olefin of Formula Id to produce a compound of the formula

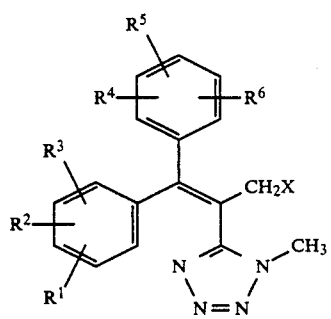
Ie wherein $R^1$, $R^2$, $R^3$, $R^4$, $R^5$, $R^6$ and X are as defined above; and (d) reacting a compound of Formula Ie with $P(OR^{10})_3$ or $P(R^{11})_3$ wherein $R^{10}$ is $C_{1-4}$ alkyl and $R^{11}$ is phenyl which is unsubstituted or substituted by one or two $C_{1-4}$ alkyl or chloro substituents, to produce a compound of the formula

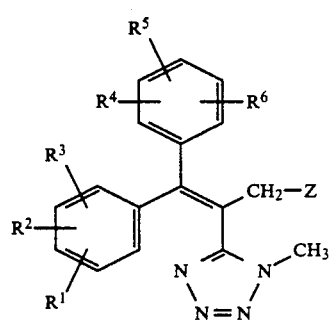

wherein $R^1$, $R^2$, $R^3$, $R^4$, $R^5$, $R^6$ and Z are as defined above.

9. A process of claim 8 wherein $R^1$, $R^2$, $R^3$, $R^4$, $R^5$ and $R^6$ each are selected from the group consisting of hydrogen, fluoro, methyl and methoxy.

10. A process of claim 9 wherein Z is triphenylphosphonium bromide.

11. A process of claim 9 wherein Z is dimethyl phosphonate.

* * * * *